(12) United States Patent
Buesing et al.

(10) Patent No.: US 8,236,968 B2
(45) Date of Patent: Aug. 7, 2012

(54) 1,4-BIS(2-THIENYLVINYL)BENZOL DERIVATIVES AND THEIR USE

(75) Inventors: Arne Buesing, Frankfurt am Main (DE); Susanne Heun, Bad Soden (DE); Aurélie Ludemann, Frankfurt (DE); Frank Egon Meyer, Hamshire (GB); Niels Schulte, Kelkheim (DE)

(73) Assignee: Merck Patent GmbH, Darmstadt (DE)

( * ) Notice: Subject to any disclaimer, the term of this patent is extended or adjusted under 35 U.S.C. 154(b) by 500 days.

(21) Appl. No.: 12/375,291

(22) PCT Filed: Jul. 5, 2007

(86) PCT No.: PCT/EP2007/005950
§ 371 (c)(1), (2), (4) Date: Jan. 27, 2009

(87) PCT Pub. No.: WO2008/011967
PCT Pub. Date: Jan. 31, 2008

(65) Prior Publication Data
US 2009/0321686 A1    Dec. 31, 2009

(30) Foreign Application Priority Data
Jul. 28, 2006    (DE) .......................... 10 2006 035 041

(51) Int. Cl.
*C07D 409/08* (2006.01)
(52) U.S. Cl. ......................................................... 549/59
(58) Field of Classification Search .................... 549/59
See application file for complete search history.

(56) References Cited

U.S. PATENT DOCUMENTS
2006/0199943 A1    9/2006    Falcou et al.

FOREIGN PATENT DOCUMENTS
| JP | 05-320635 A | 3/1993 |
| WO | WO-03/016430 A1 | 2/2003 |
| WO | WO-2004/050794 A1 | 6/2004 |
| WO | WO-2005/030827 A1 | 4/2005 |

OTHER PUBLICATIONS

Jørgensen, M., et al., "Stepwise Unidirectional Synthesis of Oligo Phenylene Vinylenes with a Series of Monomers. Use in Plastic Solar Cells," *J. Org. Chem.*, 2005, vol. 70, pp. 6004-6017.

*Primary Examiner* — Taofiq A Solola
(74) *Attorney, Agent, or Firm* — Connolly Bove Lodge & Hutz LLP

(57) ABSTRACT

The present invention relates to novel 1,4-bis(2-thienylvinyl) benzene derivatives, to conjugated polymers, dendrimers, blends, mixtures and formulations comprising same, and to the use thereof in electronic devices, in particular in polymeric organic light-emitting diodes.

18 Claims, No Drawings

1,4-BIS(2-THIENYLVINYL)BENZOL DERIVATIVES AND THEIR USE

RELATED APPLICATIONS

This application is a national stage application (under 35 U.S.C. §371) of PCT/EP2007/005950, filed Jul. 5, 2007, which claims benefit of German Application No. 10 2006 035 041.3, filed Jul. 28, 2006.

The present invention relates to novel 1,4-bis(2-thienylvinyl)benzene derivatives, to conjugated polymers, dendrimers, blends, mixtures and formulations comprising same, and to the use thereof in electronic devices, in particular in polymeric organic light-emitting diodes.

Conjugated polymers are currently being intensively investigated as highly promising materials in PLEDs (polymeric light emitting diodes). Their simple processing in contrast to SMOLEDs (small molecule organic light emitting diodes) promises less expensive production of corresponding light-emitting diodes.

Since PLEDs usually only consist of a light-emitting layer, polymers are required which are able to combine all functions of an OLED (charge injection, charge transport, recombination). Different monomers which take on the corresponding functions are therefore employed during the polymerisation. For the generation of all three emission colours, it is thus generally necessary to copolymerise certain comonomers into the corresponding polymers (cf., for example, WO 00/046321, WO 03/020790 and WO 02/077060). Thus, it is possible, for example starting from a blue-emitting base polymer ("backbone"), to generate the two other primary colours red and green.

In contrast to polymers, SMOLEDs are built up from a plurality of layers which satisfy the various functions. A light-emitting layer which comprises the emitter is also present here.

The most important criteria of an OLED are efficiency, colour and lifetime. These properties are crucially determined by the emitter(s). Although PLEDs are built up using emitters, lifetime and efficiency still remain, however, significantly behind the requirements for use in large-area displays. The materials known from the prior art for PLEDs also frequently have deficiencies with respect to the parameters of lifetime, efficiency and colour.

Surprisingly, it has been found that luminescent structures, in particular polymers and dendrimers, comprising derivatives of 1,4-bis(2-thienylvinyl)-benzene having alkyl or aryl substituents exhibit very high efficiencies and increase the lifetimes by a number of orders of magnitude compared with the reference systems to date.

WO 2005/030827 A1 describes white light-emitting polymers. On page 9, green-emitting comonomers proposed are, inter alia, vinylarylene units of a general formula IX

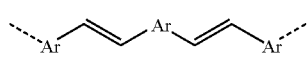

IX in which Ar is an optionally substituted aromatic or heteroaromatic ring system. These units contain at least one electron-rich ring system Ar or a ring system Ar containing electron-rich substituents, such as thiophene, furan, pyrrole or alkoxy-, aryloxy- or amino-substituted phenyl. The specific examples in WO 2005/030827 A1 disclose on page 17 a monomer of the formula M6

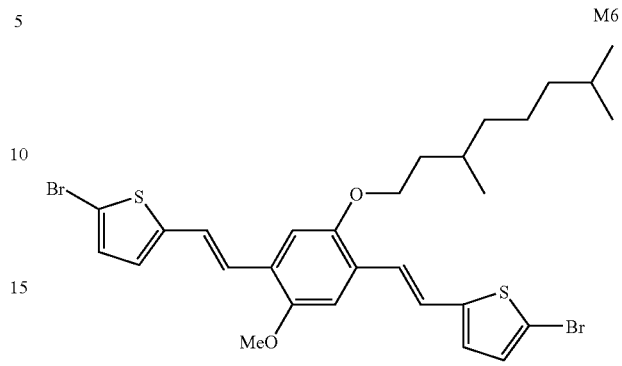

M6 containing two thiophene-2,5-diyl groups and one 1,5-dialkoxy-1,4-phenyl group. However, the compounds of the present invention are not disclosed therein.

However, the vinylarylene compounds from the prior art have some disadvantages, such as, for example, increased oxidation sensitivity in solution. It has furthermore been found that alkoxy substituents are frequently unstable to hole transport. In addition, purification of the monomer/polymer is made more difficult by the increased oxidation sensitivity. In addition, the polymers from the prior art frequently exhibit a shift in the emission colour towards yellow.

The object of the present invention was therefore, inter alia, to provide derivatives of 1,4-bis(2-thienylvinyl)benzene which do not exhibit the above-mentioned disadvantages or only do so to a reduced extent. This object has been achieved in accordance with the invention by the provision of compounds according to Claim 1

The invention thus relates to 1,4-bis(2-thienylvinyl)benzene derivatives of the formula I

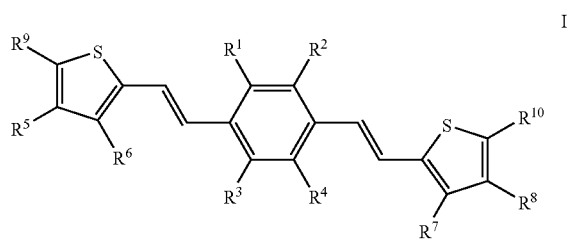

I where the symbols and indices used have the following meaning:

$R^1$ to $R^{10}$ are, independently of one another, H, $X^1$, $X^1$-Sp-, —CN, —NO$_2$, —NCS, —NCO, —OCN, —SCN, —SF$_5$, —Si(R)$_3$ or a straight-chain, branched or cyclic alkyl or alkoxy group having 1 to 22 C atoms, in which, in addition, one or more non-adjacent C atoms may be replaced by —C(R)=C(R)—, —C≡C—, —N(R)—, —O—, —S—, —CO—, —CO—O—, —O—CO—, —O—CO—O—, where, in addition, one or more H atoms may be replaced by fluorine, an aryl, aryloxy, heteroaryl or heteroaryloxy group having 5 to 40 C atoms, each of which may also be substituted by one or more non-aromatic radicals $R^{1-10}$ where, in addition, two or more of the radicals $R^{1-10}$ may form with one another an aliphatic or aromatic, mono- or poly-cyclic ring system, which may also form a condensed ring system with the benzene ring or the thiophene rings in the formula I, or denote a link in the polymer, R is on each occurrence, identically or differently, H, halogen, a straight-chain, branched or cyclic alkyl chain having 1 to 22 C atoms, in which, in addition, one or more non-adjacent C atoms may be replaced by —O—S—, —CO—, —CO—O—, —O—CO—, —O—CO—O—, where, in addition, one or more H atoms may be replaced by fluorine, an aryl, aryloxy, heteroaryl or heteroaryloxy group having 5 to 40 C atoms, which may also be substituted by one or more non-aromatic radicals $R^{1-10}$; a plurality of radicals R with one another and/or with further radicals $R^{1-10}$ may also form an aromatic or aliphatic, mono- or polycyclic ring system, which may also form a condensed ring system with the benzene ring or the thiophene rings in the formula I, $X^1$ is on each occurrence, identically or differently, a reactive group, Sp is on each occurrence, identically or differently, a spacer group or a single bond, in which at least one of the radicals $R^1$ to $R^4$ denotes an optionally substituted alkyl, aryl or heteroaryl group.

The present invention furthermore relates to polymers or dendrimers, preferably conjugated polymers or dendrimers, obtainable by polymerisation of one or more compounds of the formula I, optionally with additional comonomers.

The present invention furthermore relates to a mixture, preferably consisting of low-molecular-weight components, comprising one or more compounds of the formula I and additionally one or more light-emitting and/or polymerisable compounds.

The present invention furthermore relates to a polymer blend comprising one or more polymers or dendrimers according to the invention and optionally comprising one or more further polymeric, oligomeric, dendritic or low-molecular-weight substances.

The present invention furthermore relates to a formulation comprising
one or more compounds of the formula I or polymers, dendrimers, polymer blends or low-molecular-weight mixtures obtainable therefrom,
one or more solvents and/or one or more polymeric binders.

The present invention furthermore relates to the use of the compounds, polymers, dendrimers, mixtures and formulations according to the invention in electronic or electro-optical devices, in particular in organic or polymeric organic light-emitting diodes (OLEDs, PLEDs), organic field-effect transistors (OFETs), organic integrated circuits (O-ICs), organic thin-film transistors (O-TFTs), organic solar cells (O-SCs), organic laser diodes (O-lasers), organic photovoltaic (OPV) elements or devices or organic photoreceptors (OPCs).

The terms "alkyl", "aryl", "heteroaryl", etc., also encompass polyvalent groups, for example alkylene, arylene, heteroarylene, etc.

Above and below, the term "carbon radical" denotes a mono- or polyvalent organic radical containing at least one carbon atom which either contains no further atoms (such as, for example, —C≡C—) or optionally contains one or more further atoms, such as, for example, N, O, S, P, Si, Se, As, Te or Ge (for example carbonyl, etc.). The term "hydrocarbon radical" denotes a carbon radical which additionally contains one or more H atoms and optionally one or more heteroatoms, such as, for example, N, O, S, P, Si, Se, As, Te or Ge.

The term "aryl" denotes an aromatic carbon group or a group derived therefrom. The term "heteroaryl" denotes "aryl" in accordance with the above definition containing one or more heteroatoms.

A carbon or hydrocarbon radical may be a saturated or unsaturated group. Unsaturated groups are, for example, aryl, alkenyl or alkynyl groups. A carbon or hydrocarbon radical having more than 3 C atoms may be straight-chain, branched and/or cyclic and may also have spiro links or condensed rings.

Preferred carbon and hydrocarbon radicals are optionally substituted alkyl, alkenyl, alkynyl, alkoxy, alkylcarbonyl, alkoxycarbonyl, alkylcarbonyloxy and alkoxycarbonyloxy having 1 to 40, preferably 1 to 25, particularly preferably 1 to 18, C atoms, optionally substituted aryl or aryloxy having 6 to 40, preferably 6 to 25, C atoms, or optionally substituted alkylaryl, aryl-alkyl, alkylaryloxy, arylalkyloxy, arylcarbonyl, aryloxycarbonyl, arylcarbonyloxy and aryloxycarbonyloxy having 6 to 40, preferably 6 to 25, C atoms.

Further preferred carbon and hydrocarbon radicals are $C_1$-$C_{40}$ alkyl, $C_2$-$C_{40}$ alkenyl, $C_2$-$C_{40}$ alkynyl, $C_3$-$C_{40}$ alkyl, $C_4$-$C_{40}$ alkyldienyl, $C_4$-$C_{40}$ polyenyl, $C_6$-$C_{40}$ aryl, $C_6$-$C_{40}$ alkylaryl, $C_6$-$C_{40}$ arylalkyl, $C_6$-$C_{40}$ alkylaryloxy, $C_6$-$C_{40}$ arylalkyloxy, $C_6$-$C_{40}$ heteroaryl, $C_4$-$C_{40}$ cycloalkyl, $C_4$-$C_{40}$ cycloalkenyl, etc. Particular preference is given to $C_1$-$C_{22}$ alkyl, $C_2$-$C_{22}$ alkenyl, $C_2$-$C_{22}$ alkynyl, $C_3$-$C_{22}$ allyl, $C_4$-$C_{22}$ alkyldienyl, $C_6$-$C_{12}$ aryl, $C_6$-$C_{20}$ arylalkyl and $C_6$-$C_{20}$ heteroaryl.

Further preferred carbon and hydrocarbon radicals are straight-chain, branched or cyclic alkyl radicals having 1 to 40, preferably 1 to 22, C atoms, which are unsubstituted or mono- or polysubstituted by F, Cl, Br, I or CN and in which one or more non-adjacent $CH_2$ groups may each be replaced, independently of one another, by —C(R)=C(R)—, —C≡C—, —N(R)—, —O—, —S—, —CO—, —CO—O—, —O—CO—, —O—CO—O— in such a way that O and/or S atoms are not linked directly to one another, where R has the meaning indicated above.

Preferred alkyl groups are, for example, methyl, ethyl, n-propyl, isopropyl, n-butyl, isobutyl, s-butyl, t-butyl, 2-methylbutyl, n-pentyl, s-pentyl, cyclo-pentyl, n-hexyl, cyclohexyl, 2-ethylhexyl, n-heptyl, cycloheptyl, n-octyl, cyclooctyl, dodecanyl, trifluoromethyl, perfluoro-n-butyl, 2,2,2-trifluoroethyl, perfluorooctyl, perfluorohexyl, etc.

Preferred alkenyl groups are, for example, ethenyl, propenyl, butenyl, pentenyl, cyclopentenyl, hexenyl, cyclohexenyl, heptenyl, cycloheptenyl, octenyl, cyclooctenyl, etc.

Preferred alkynyl groups are, for example, ethynyl, propynyl, butynyl, pentynyl, hexynyl, octynyl, etc.

Preferred alkoxy groups are, for example, methoxy, ethoxy, 2-methoxyethoxy, n-propoxy, i-propoxy, n-butoxy, i-butoxy, s-butoxy, t-butoxy, 2-methylbutoxy, n-pentoxy, n-hexoxy, n-heptoxy, n-octoxy, etc.

Preferred amino groups are, for example, dimethylamino, methylamino, methylphenylamino, phenylamino, etc.

Aryl groups may be monocyclic or polycyclic, i.e. they may have one ring (for example phenyl) or two or more rings, which may also be condensed (for example naphthyl) or covalently linked (for example biphenyl), or contain a combination of condensed and linked rings. Preference is given to fully conjugated aryl groups.

Preferred aryl groups are, for example, phenyl, biphenyl, triphenyl, 1,1':3',1''-terphenyl-2'-yl, naphthyl, anthracene, binaphthyl, phenanthrene, pyrene, dihydropyrene, chrysene, perylene, tetracene, pentacene, benzopyrene, fluorene, indene, indenofluorene, spirobifluorene, etc.

Preferred heteroaryl groups are, for example, 5-membered rings, such as pyrrole, pyrazole, imidazole, 1,2,3-triazole, 1,2,4-triazole, tetrazole, furan, thiophene, selenophene, oxazole, isoxazole, 1,2-thiazole, 1,3-thiazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 6-membered rings, such as pyridine, pyridazine, pyrimidine, pyrazine, 1,3,5-triazine, 1,2,4-triazine, 1,2,3-triazine, 1,2,4,5-tetrazine, 1,2,3,4-tetrazine, 1,2,3,5-tetrazine, or condensed groups, such as indole, isoindole, indolizine, indazole, benzimidazole, benzotriazole, purine, naphthimidazole, phenanthrimidazole, pyridimidazole, pyrazinimidazole, quinoxalinimidazole, benzoxazole, naphthoxazole, anthroxazole, phenanthroxazole, isoxazole, benzothiazole, benzofuran, isobenzofuran, dibenzofuran, quinoline, isoquinoline, pteridine, benzo-5,6-quinoline, benzo-6,7-quinoline, benzo-7,8-quinoline, benzoisoquinoline, acridine, phenothiazine, phenoxazine, benzopyridazine, benzopyrimidine, quinoxaline, phenazine, naphthyridine, azacarbazole, benzocarboline, phenanthridine, phenanthroline, thieno[2,3b]-thiophene, thieno[3,2b]thiophene, dithienothiophene, isobenzothiophene, dibenzothiophene, benzothiadiazothiophene, or combinations of these groups. The heteroaryl groups may also be substituted by alkyl, alkoxy, thioalkyl, fluorine, fluoroalkyl or other aryl or heteroaryl groups.

The aryl, heteroaryl, carbon and hydrocarbon radicals optionally have one or more substituents, which are preferably selected from the group consisting of silyl, sulfo, sulfonyl, formyl, amine, imine, nitrile, mercapto, nitro, halogen, $C_{1-12}$ alkyl, $C_{6-12}$ aryl, $C_{1-12}$ alkoxy, hydroxyl or combinations of these groups.

Preferred substituents are, for example, solubility-promoting groups, such as alkyl or alkoxy, electron-withdrawing groups, such as fluorine, nitro or nitrile, or substituents for increasing the glass-transition temperature (Tg) in the polymer, in particular bulky groups, such as, for example, t-butyl or optionally substituted aryl groups.

Particularly preferred substituents, also referred to as "L" below, are, for example, F, Cl, Br, I, —CN, —$NO_2$, —NCO, —NCS, —OCN, —SCN, —C(=O)N(R)$_2$, —C(=O)Y$^1$, —O(=O)R, —N(R)$_2$, in which R has the meaning indicated above and Y$^1$ denotes halogen, optionally substituted silyl, aryl having 4 to 40, preferably 6 to 20, C atoms, and straight-chain or branched alkyl, alkoxy, alkylcarbonyl, alkoxycarbonyl, alkylcarbonyloxy or alkoxycarbonyloxy having 1 to 22 C atoms, in which one or more H atoms may optionally be replaced by F or Cl.

In a first preferred embodiment, $X^1$ denotes a group which is suitable for a polymerisation reaction with C—C, C—N or C—O linking, such as, for example, the SUZUKI, YAMAMOTO, STILLE, Buchwald, Kumada or Sonogashira polymerisations below.

Preferred groups $X^1$ of this first type are halogen, in particular Br, Cl or I, furthermore —OH, —COOH, —CY$_1$O, —CHO, —$CH_2Cl$, —N(R$^0$)$_2$, —Si(R$^0$)$_3$, —Sn(R$^0$)$_3$, —B(R$^0$)$_2$, —B(OR$^0$)$_2$, —B(OH)$_2$, —OR$^0$=C(R$^0$)$_2$, —C≡CH, —O—$SO_2$R$^0$, —SiMe$_2$F or —SiMeF$_2$, in which Y$^1$ denotes halogen, Me denotes methyl and R$^0$ denotes optionally substituted alkyl or aryl, where, in addition, two groups R$^0$ may form an aromatic or aliphatic, mono- or polycyclic ring system. Preferred groups —O—$SO_2$R$^0$ are, in particular, O-tosylate, O-triflate, O-mesylate and O-nonaflate.

In a second preferred embodiment, $X^1$ denotes a group which is suitable for a polymerisation reaction, such as, for example, free-radical or ionic chain polymerisation, polyaddition or polycondensation, or for a polymer-analogous reaction, for example the addition or condensation onto a polymer main chain. Particular preference is given to groups for chain polymerisation, in particular those containing a C—C double bond or C—C triple bond, and groups which are suitable for polymerisation with ring opening, such as, for example, oxetane or epoxide groups.

Preferred groups $X^1$ of this second type are selected from $CH_2$=$CW^1$—COO—, $CH_2$=$CW^1$—CO—,

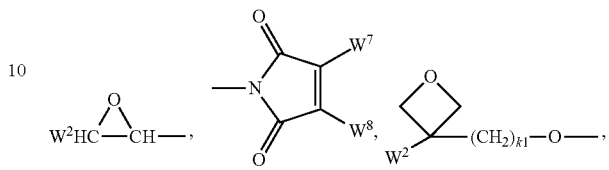

$CH_2$=$CW^2$—(O)$_{k1}$—, $CH_3$—CH=CH—O—, $(CH_2$=$CH)_2$—CH—OCO—, $(CH_2$=$CH$—$CH_2)_2$CH—OCO—, $(CH_2$=$CH)_2$CH—O—, $(CH_2$=$CH$—$CH_2)_2$N—, $(CH_2$=$CH$—$CH_2)_2$N—CO—, HO—$CW^2W^3$—, HS—$CW^2W^3$—, HW$^2$N—, HO—$CW^2W^3$—NH—, $CH_2$=$CW^1$—CO—NH—, $CH_2$=$CH$—$(COO)_{k1}$-Phe-(O)$_{k2}$—, $CH_2$=$CH$—$(CO)_{k1}$-Phe-(O)$_{k2}$—, Phe-CH=CH—, HOOC—, OCN— and $W^4W^5W^6$Si—, in which $W^1$ denotes H, F, Cl, CN, $CF_3$, phenyl or alkyl having 1 to 5 C atoms, in particular H, $C_1$ or $CH_3$, $W^2$ and $W^3$ each, independently of one another, denote H or alkyl having 1 to 5 C atoms, in particular H, methyl, ethyl or n-propyl, $W^4$, $W^5$ and $W^6$ each, independently of one another, denote Cl, oxaalkyl or oxacarbonylalkyl having 1 to 5 C atoms, $W^7$ and $W^8$ each, independently of one another, denote H, Cl or alkyl having 1 to 5 C atoms, Phe denotes 1,4-phenylene, which is optionally substituted by one or more radicals L as defined above, and $k_1$ and $k_2$ each, independently of one another, denote 0 or 1.

Particularly preferred groups $X^1$ of this second type are $CH_2$=CH—COO—, $CH_2$=C(CH$_3$)—COO—, $CH_2$=CH—, $CH_2$—CH—O—, $(CH_2$—CH)$_2$CH—OCO—, $(CH_2$=$CH)_2$CH—O—,

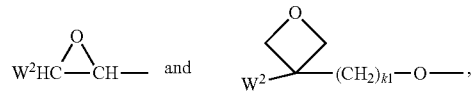

in particular vinyl, acrylate, methacrylate, oxetane and epoxide.

The term "spacer group" (Sp) is known to the person skilled in the art and is described in the literature, see, for example, Pure Appl. Chem. 73(5), 888 (2001).

Preferred spacer groups Sp are selected from the formula Sp'-X', so that "$X^1$-Sp-" denotes "$X^1$-Sp'-X'-", where Sp' denotes alkylene having 1 to 20, preferably 1 to 12, C atoms, which is optionally mono- or polysubstituted by F, Cl, Br, I or CN and in which, in addition, one or more non-adjacent $CH_2$ groups may each be replaced, independently of one another, by —O—, —S—, —NH—, —NR$^0$—, —SiR$^0$R$^{00}$—, —CO—, —CO—, —OCO—, —OCO—O—, —S—CO—, —CO—S—, —NR$^0$—CO—O—, —O—CO—NR$^0$—, —NR$^0$—CO—NR$^0$—, —CH=CH— or —C≡C— in such a way that O and/or S atoms are not linked directly to one another, X' denotes —O—, —S—, —CO—, —COO—, —OCO—, —O—COO—, —CO—NR$^0$—, —NR$^0$—CO—, —NR$^0$—CO—NR$^0$—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR⁰—, —CY²=CY³—, —C≡C—, —CH=CH—COO—, —OCO—CH=CH— or a single bond, R⁰ and R⁰⁰ each, independently of one another, denote H or alkyl having 1 to 12 C atoms, and Y² and Y³ each, independently of one another, denote H, F, Cl or CN.

X' is preferably —O—, —S—, —CO—, —COO—, —OCO—, —O—COO—, —CO—NR⁰—, —NR⁰—CO—, —NR⁰—CO—NR⁰— or a single bond.

Typical spacer groups Sp' are, for example, —(CH₂)ₚ—, —(CH₂CH₂O)_q—CH₂CH₂—, —CH₂CH₂—S—CH₂CH₂—, —CH₂CH₂—NH—CH₂CH₂— or —(SiR⁰R⁰⁰—O)ₚ—, in which p is an integer from 2 to 12, q is an integer from 1 to 3, and R⁰ and R⁰⁰ have the above-mentioned meanings.

Particularly preferred groups Sp' are, for example, in each case straight-chain ethylene, propylene, butylene, pentylene, hexylene, heptylene, octylene, nonylene, decylene, undecylene, dodecylene, octadecylene, ethyleneoxyethylene, methyleneoxybutylene, ethylenethioethylene, ethylene-N-methyliminoethylene, 1-methylalkylene, ethenylene, propenylene and butenylenes.

"Halogen" denotes F, Cl, Br or I.

For the purposes of this invention, "conjugated polymers" are polymers which contain principally sp²-hybridised (or optionally also sp-hybridised) carbon atoms, which may also be replaced by corresponding hetero-atoms, in the main chain. In the simplest case, this means the alternating presence of double and single bonds in the main chain, but also polymers containing units such as, for example, meta-linked phenylene are intended to be regarded as conjugated polymers for the purposes of this invention.

"Principally" means that naturally (randomly) occurring defects which result in conjugation interruptions do not devalue the term "conjugated polymer". Furthermore, the term "conjugated" is likewise used in this application text if the main chain contains, for example, arylamine units, arylphosphine units and/or certain heterocycles (i.e. conjugation via N, O, P or S atoms) and/or organometallic complexes (i.e. conjugation via the metal atom). An analogous situation applies to conjugated dendrimers.

This invention also relates to partially conjugated polymers. For the purposes of this invention, the term "partially conjugated polymer" signifies polymers which contain conjugated regions which are separated from one another by non-conjugated sections, specific conjugation interrupters (for example spacer groups, Sp) or branches. Conjugated and partially conjugated polymers may also contain conjugated, partially conjugated or other dendrimers.

The term "dendrimer" here is intended to be taken to mean a highly branched compound which is built up from a multi-functional centre (core) to which branched monomers are bonded in a regular construction, giving a tree-like structure. Both the core and also the monomers here can adopt any desired branched structures which consist both of purely organic units and also organometallic compounds or coordination compounds. "Dendrimer" here is in general intended to be understood as described, for example, by M. Fischer and F. Vögtle (*Angew. Chem., fn. Ed.* 1999) 38, 885).

Aryl(oxy) and heteroaryl(oxy) radicals are preferably mono- or polysubstituted by L as defined above.

A preferred embodiment of the invention is directed to compounds of the formula I in which at least two of the radicals R¹ to R¹⁰, particularly preferably the radicals R⁹ and R¹⁰, denote a leaving group X¹ as defined above. Such compounds are suitable as monomers for the preparation of conjugated polymers and dendrimers according to the invention. A monomer of the formula I can be converted into homopolymers or reacted with other monomers of the formula I or further monomers to give copolymers. Preference is given here to the exclusive use of monomers which result in fully conjugated polymers.

A further preferred embodiment of the invention is directed to compounds of the formula I in which one or more radicals R¹ to R¹⁰ or R denote a group P-Sp- as defined above or denote a group which has at least one substituent P-Sp-. Polymerisation or polymer-analogous reaction of the group P in such compounds enables the preparation of non-conjugated, linear or crosslinked polymers which have structures of the formula I in their polymer main chain or side chain. Correspondingly, reaction of the groups X¹ in monomers which contain both leaving groups X¹ and also reactive groups P firstly enables the preparation of conjugated oligomers or polymers, which are then crosslinked by reaction of the group P.

Particular preference is given to compounds of the formula I in which one, two, three or four of the radicals R¹⁴ denote an optionally substituted alkyl group having 1 to 22 C atoms or an optionally substituted aryl or heteroaryl group having 5 to 40 C atoms, and the other radicals R¹⁴ denote H.

Preference is furthermore given to compounds of the formula I in which all radicals R¹⁻⁴ are different from H, R¹ is different from H and R²⁻⁴ denote H, R¹ and R² are different from H and R³ and R⁴ denote H, R¹ and R⁴ are different from H and R² and R³ denote H, all radicals R¹⁻⁴ which are different from H denote an optionally substituted alkyl, aryl or heteroaryl group, the radicals R¹⁻⁴ which are different from H denote optionally fluorinated straight-chain, branched or cyclic alkyl having 1 to 22 C atoms, the radicals R¹⁻⁴ which are different from H denote phenyl or 1-naphthyl, each of which is optionally substituted by one or more, preferably 1, 2 or 3, radicals L, a phenyl radical is preferably substituted by L in the 2 and/or 5-position, a 1-naphthyl radical is preferably substituted by L in the 4-position, R⁹ and R¹⁰ each, independently of one another, have one of the meanings indicated for X¹.

Very particular preference is given to compounds of the formula I selected from the following sub-formulae:

(Ia)

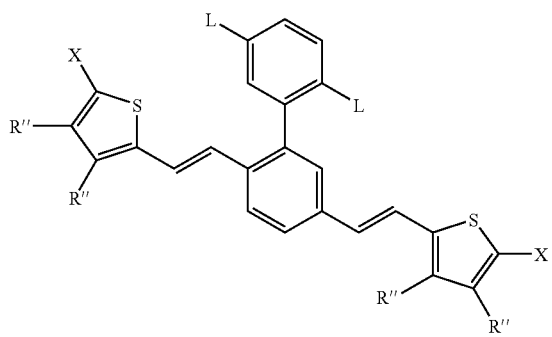

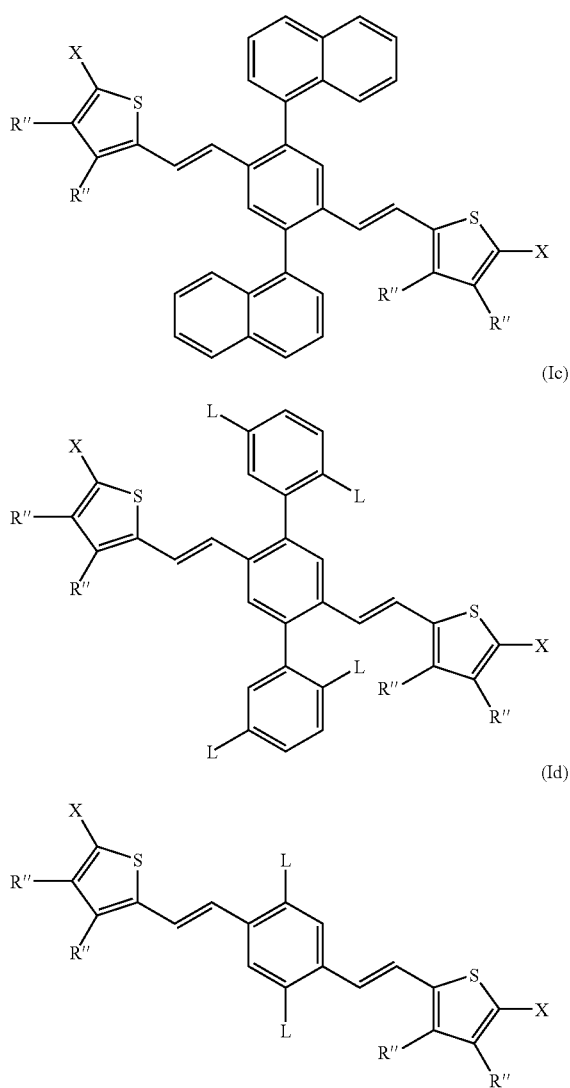

in which X has one of the meanings indicated for $X^1$, R" has one of the meanings indicated for $R^{5-8}$, and L has one of the above-mentioned meanings. L in these sub-formulae preferably denotes straight-chain or branched alkyl or fluoroalkyl having 1 to 22, particularly preferably 1 to 12, C atoms.

The compounds of the formula I are readily accessible in high yields. They exhibit intense green luminescence in the solid state.

The compounds of the formula I can be prepared by methods known to the person skilled in the art and described in the literature. Further suitable preferred synthetic processes are given in the examples. The present invention furthermore relates to the processes described therein.

The compounds according to the invention and polymers and dendrimers prepared therefrom have improved properties compared with the materials in accordance with the prior art, in particular significantly improved lifetimes, high efficiencies and better colour coordinates.

In accordance with the invention, the compounds of the formula I can be incorporated into the main chain or side chain of a polymer. In the case of incorporation into the side chain, it is possible for the compound of the formula I to be in conjugation with the polymer main chain or to be none conjugated with the polymer main chain.

If the compounds of the formula I are used for the synthesis of polymers according to the invention, the linking in the polymer preferably takes place via the groups $R^9$ and $R^{10}$. For linking reactions of this type, use is preferably made of monomers of the formula I in which $R^9$ and $R^{10}$ have one of the meanings indicated for $X^1$. The groups $R^{9/10}$ and $X^1$ are eliminated during this linking.

In the following description of the polymers according to the invention, the compounds of the formula I are also referred to as "structural units of the formula I" or "units of the formula I", where $R^9$ and $R^{10}$ and, in the case of linking via other positions, analogously the radicals $R^1$ to $R^8$, are intended to denote a link in the polymer.

In a preferred embodiment of the invention, units of the formula I are in conjugation with the polymer main chain. This can be achieved on the one hand by incorporating these units into the main chain of the polymer in such a way that the conjugation of the polymer, as described above, is thereby retained. On the other hand, these units can also be linked into the side chain of the polymer in such a way that conjugation with the main chain of the polymer exists. This is the case, for example, if the linking to the main chain takes place only via $sp^2$-hybridised (or optionally also via sp-hybridised) carbon atoms, which may also be replaced by corresponding heteroatoms. However, if the linking takes place through units such as, for example, simple (thio)ether bridges, esters, amides or alkylene chains, the units of the formula I are defined as non-conjugated with the main chain.

Conjugated or partially conjugated polymers and dendrimers according to the invention preferably contain 0.01 to 25 mol % of one or more units of the formula I. The amount to be employed depends on the polymer colour to be achieved. For single-coloured polymers, 0.8 to 20 mol %, particularly preferably 1 to 15 mol %, are preferred. For multicoloured polymers, the proportions are lower, preferably below 1.5 mol %, particularly preferably below 1 mol %.

Particular preference is given to polymers according to the invention which also contain further structural elements in addition to units of the formula I and should thus be regarded as copolymers. Although the further comonomers are necessary for the synthesis of the copolymers according to the invention, they are, however, not themselves a subject-matter of the present invention and should thus be described by reference. Reference should also be made here, in particular, to the relatively extensive lists in WO 02/077060, WO 2005/014689 and the references cited therein.

These further structural units can originate, for example, from the classes described below:
Group 1: Comonomers which represent the polymer backbone.
Group 2: Comonomers which increase the hole-injection and/or -transport properties of the polymers.
Group 3: Comonomers which increase the electron-injection and/or -transport properties of the polymers.
Group 4: Comonomers which have combinations of individual units from group 2 and group 3.

Suitable and preferred units for the above-mentioned groups are described below.

Group 1—comonomers which represent the polymer backbone:
Preferred units from group 1 are, in particular, those which contain aromatic or carbocyclic structures having 6 to 40 C atoms. Suitable and preferred units are, inter alia, fluorene derivatives, as disclosed, for example, in EP 0 842 208, WO 99/54385, WO 00/22027, WO 00/22026 or WO 00/46321, furthermore spirobifluorene derivatives, as disclosed, for example, in EP 0 707 020, EP 0 894 107 and WO 03/020790, or dihydro-phenanthrene derivatives, as disclosed in WO 2005/014689. It is also possible to use a combination of two or more of these monomer units, as described, for example, in WO 02/077060. Other structural elements which are able to influence the morphology, but also the emission colour of the resultant polymers are also possible. Preference is given here to substituted or unsubstituted aromatic structures which have 6 to 40 C atoms, or also stilbene or bisstyrylarylene derivatives, such as, for example, 1,4-phenylene, 1,4-naphthylene, 1,4- or 9,10-anthrylene, 1,6- or 2,7- or 4,9-pyrenylene, tetrahydropyrenylene, 3,9- or 3,10-perylenylene, 2,7- or 3,6-phenanthrenylene, 4,4'-biphenylylene, 4,4"-terphenylylene, 4,4'-bi-1,1'-naphthylylene, 4,4'-stilbenzyl or 4,4"-bisstyrylarylene derivatives.

Preferred units for the polymer backbone are spirobifluorenes, indenofluorenes, phenanthrenes and dihydrophenanthrenes.

Particularly preferred units from group 1 are divalent units of the following formulae, in which the dashed line denotes the link to the adjacent unit:

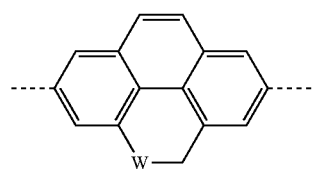
(Ia)

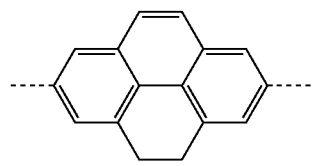
(Ib)

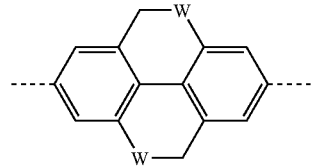
(Ic)

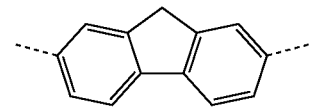
(II)

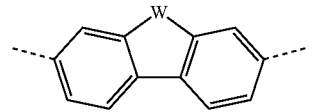
(III)

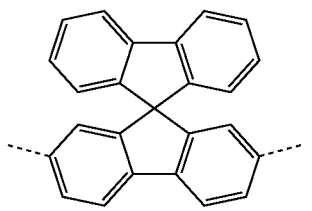
(IVa)

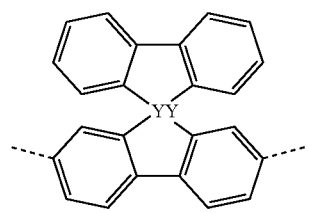
(IVb)

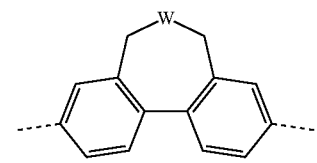
(V)

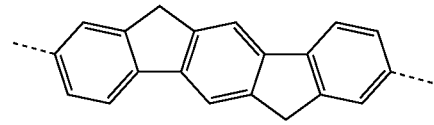
(VI)

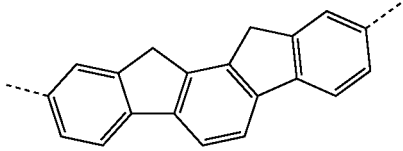
(VII)

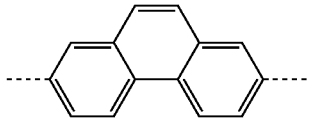
(VIII)

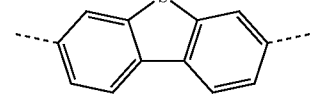
(IX)

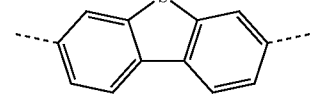
(X)

where the various positions may also be substituted by one or more substituents $R^5$ as defined above, YY denotes Si or Ge, and VV denotes O, S or Se.

Group 2—comonomers which increase the hole-injection and/or -transport properties of the polymers:

These are generally aromatic amines or electron-rich heterocycles, such as, for example, substituted or unsubstituted triarylamines, benzidines, tetraarylene-para-phenylenediamines, phenothiazines, phenoxazines, dihydrophenazines, thianthrenes, dibenzo-p-dioxins, phenoxathiynes, carbazoles, azulenes, thiophenes, pyrroles, furans and further O-, S- or N-containing heterocycles having a high HOMO (HOMO=highest occupied molecular orbital). However, triarylphosphines as described in WO 2005/017065 are also suitable here.

Particularly preferred units from group 2 are divalent units of the following formulae, in which the dashed line denotes the link to the adjacent unit:

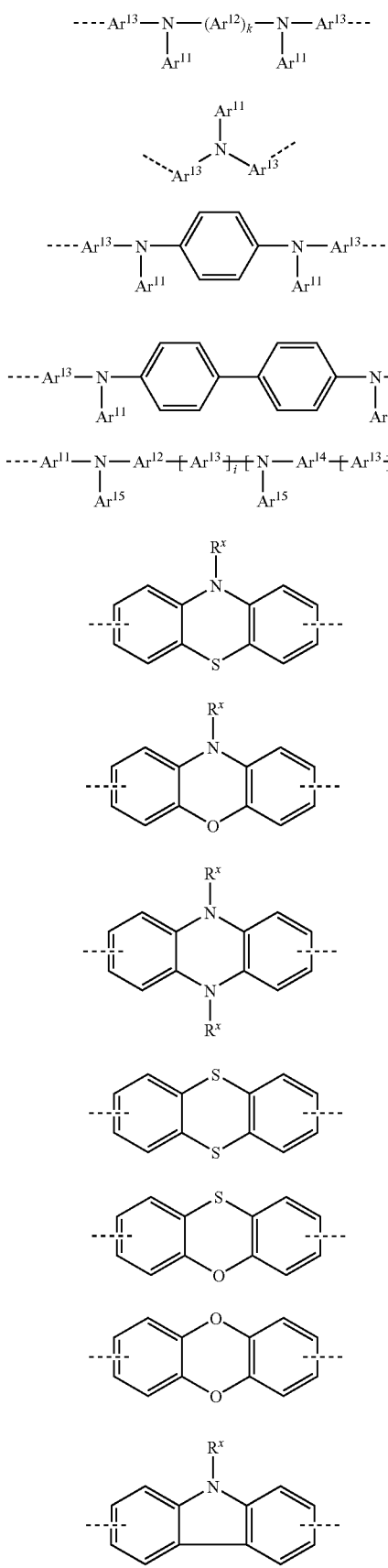

where $R^x$ has one of the above-mentioned meanings for $R^1$, the various formulae may also additionally be substituted in the free positions by one or more substituents $R^x$, and the other symbols and indices have the following meaning:

i is, identically or differently on each occurrence, 0, 1 or 2, k is, identically or differently on each occurrence, 0, 1 or 2, preferably 0 or 1, l is, identically or differently on each occurrence, 1, 2 or 3, preferably 1 or 2, $Ar^{11}$, $Ar^{13}$ are on each occurrence, identically or differently, an aromatic or heteroaromatic ring system having 2 to 40 C atoms, which may be mono- or polysubstituted by $R^x$ or also unsubstituted; the possible substituents $R^x$ here may potentially be in any free position, $Ar^{12}$, $Ar^{14}$ are on each occurrence, identically or differently, $Ar^{11}$, $Ar^{13}$ or a substituted or unsubstituted stilbenzylene or tolanylene unit, $Ar^{15}$ is, identically or differently on each occurrence, either a system as described by $Ar^{11}$ or an aromatic or heteroaromatic ring system having 9 to 40 aromatic atoms (C or heteroatoms), which may be mono- or polysubstituted by $R^x$ or unsubstituted and which consists of at least two condensed rings; the possible substituents $R^x$ here may potentially be in any free position.

Group 3—comonomers which significantly increase the electron-injection and/or -transport properties of the polymers:

These are generally electron-deficient aromatics or heterocycles, such as, for example, substituted or unsubstituted pyridines, pyrimidines, pyridazines, pyrazines, anthracenes, oxadiazoles, quinolines, quinoxalines or phenazines, but also compounds such as triarylboranes and further O—, S— or N-containing heterocycles having a low LUMO (LUMO=lowest unoccupied molecular orbital), and benzophenones and derivatives thereof, as disclosed, for example, in WO 05/040302.

Particularly preferred units from group 3 are divalent units of the following formulae, in which the dashed line denotes the link to the adjacent unit:

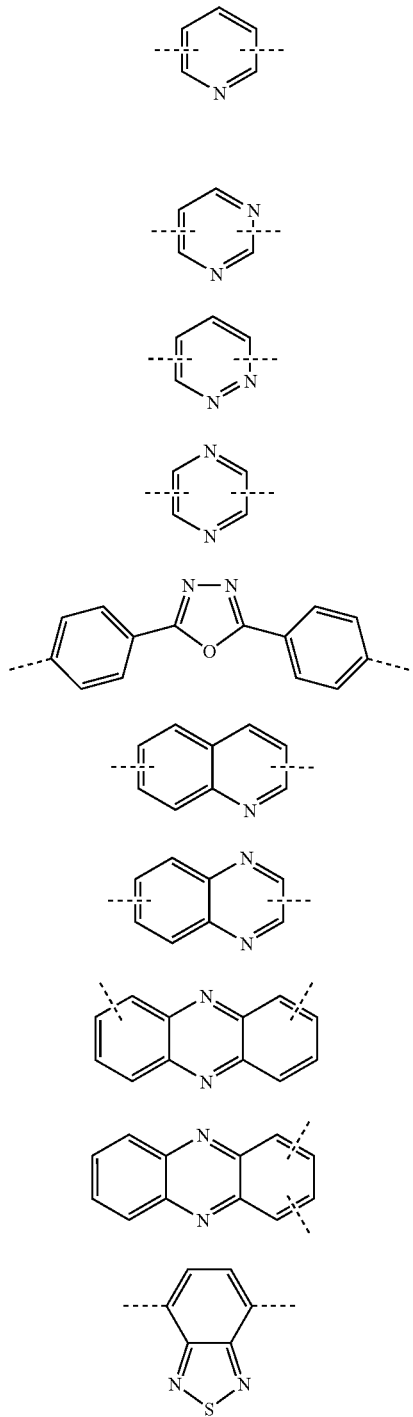

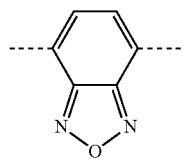

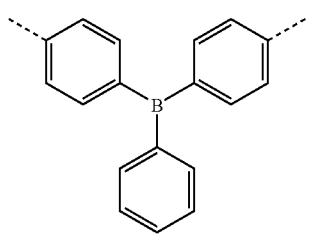

where the various formulae may be substituted in the free positions by one or more substituents $R^x$ as defined above.

Group 4—comonomers which have combinations of individual units from group 2 and group 3:

It is also possible for the polymers according to the invention to contain units in which structures which increase the hole mobility and the electron mobility are bonded directly to one another. However, some of these units shift the emission colour into the yellow or red. Their use in polymers according to the invention for the generation of blue or green emission is therefore less preferred.

If such units from group 4 are present in the polymers according to the invention, they are preferably selected from divalent units of the following formulae, in which the dashed line denotes the link to the adjacent unit:

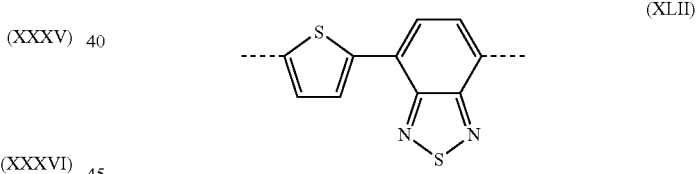

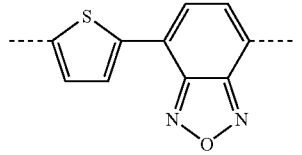

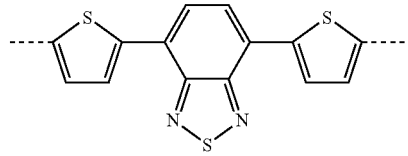

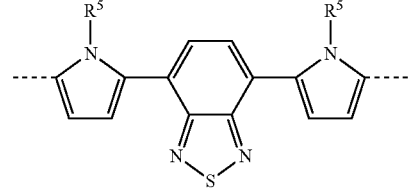

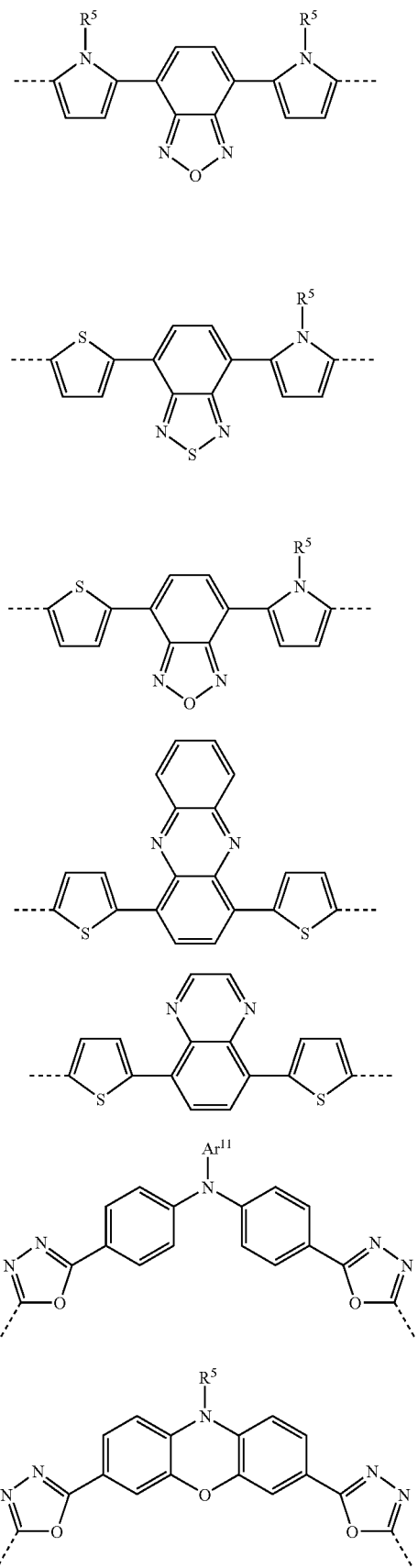

where the various formulae may be substituted in the free positions by one or more substituents $R^x$ as defined above, the symbols $R^x$, $Ar^{11}$, k and l have the above-mentioned meaning, and $Y^o$ is on each occurrence, identically or differently, O, S, Se, N, P, Si or Ge.

It is also possible for more than one structural unit from one of groups 1 to 4 to be present simultaneously.

The polymer according to the invention may furthermore likewise contain metal complexes, which are generally built up from one or more ligands and one or more metal centres, bonded into the main or side chain.

Preference is given to polymers according to the invention which, besides units of the formula I, additionally also contain one or more units selected from groups 1 to 4.

Preference is given here to polymers according to the invention which, besides units of the formula I, also contain units from group 1, particularly preferably at least 50 mol % of these units.

It is likewise preferred for the polymers according to the invention to contain units which improve the charge transport or charge injection, i.e. units from group 2 and/or 3; a proportion of 2 to 30 mol % of these units is particularly preferred; a proportion of 2 to 10 mol % of these units is very particularly preferred.

It is furthermore particularly preferred for the polymers according to the invention to contain units from group 1 and units from group 2 and/or 3, in particular at least 50 mol % of units from group 1 and 2 to 30 mol % of units from group 2 and/or 3.

The polymers according to the invention preferably have 10 to 10,000, particularly preferably 20 to 5000 and in particular 50 to 2000, recurring units. Corresponding dendrimers may also have fewer recurring units.

The requisite solubility of the polymers and dendrimers is ensured, in particular, by the substituents on the various recurring units, both by substituents $R^{1-10}$ on the compounds of the formula I and also by substituents on the other recurring units.

The polymers according to the invention are either homopolymers comprising units of the formula I or copolymers. The polymers according to the invention may be linear or branched (crosslinked). Besides one or more units of the formula I, or preferred sub-formulae thereof, copolymers according to the invention may potentially have one or more further structures from groups 1 to 4 mentioned above.

The copolymers according to the invention may have random, alternating or block-like structures or also have a plurality of these structures in an alternating arrangement. The way in which copolymers having block-like structures can be obtained and which further structural elements are particularly preferred for this purpose are described in detail, for example, in WO 2005/014688. This is incorporated into the present application by way of reference. It should likewise be re-emphasised at this point that the polymer may also have dendritic structures.

Compounds of the formula I can also be used as green-emitting comonomers for the synthesis of red-emitting polymers. The invention thus furthermore relates to the use of compounds of the formula I for the synthesis of red-emitting polymers.

It may also be preferred for a significantly smaller proportion than 1 mol % of compounds of the formula I to be used. Thus, 0.01 to 1 mol % of such compounds, for example as blue- or green-emitting units, can be used for the synthesis of white-emitting copolymers. For this purpose, only a small proportion of blue- or green-emitting units is generally required, as described in WO 2005/030828. The invention thus also relates to the use of compounds of the formula I for the synthesis of white-emitting copolymers.

White-emitting copolymers according to the invention preferably contain at least three different recurring units, where the first recurring unit, unit A, is usually present in a proportion of at least 10 mol % and exhibits blue emission, the second recurring unit, unit G, is usually present in the polymer in a proportion of 0.001 to 3 mol % and exhibits green emission, and the third recurring unit, unit R, is usually present in a proportion of 0.0005 to 1 mol % and exhibits red emission. The green recurring unit here is a unit of the formula I. However, a plurality of units R, G and B may also be present, but where at least one of the units G conforms to the formula I.

White emission is defined by the CIE colour coordinates x=0.33 and y=0.33 (chromaticity coordinates of the Commission Internationale de l'Eclairage from 1931). However, the colour impression may vary individually, meaning that a value which is in the vicinity of this range may also still leave the impression of white emission. For the purposes of this invention, white emission is intended to be taken to mean an emission whose colour coordinates are within an ellipse defined by the points having x/y colour coordinates of about (0.22/0.24), (0.46/0.44), (0.28/0.38) and (0.37/0.28).

For the purposes of this application, a blue-emitting recurring unit B is defined in such a way that a film of the homopolymer of this unit B exhibits luminescence (fluorescence or phosphorescence) and that the maximum of the emission curve of a film of a polymer which contains 10 mol % of this unit B and 90 mol % of 2,7-[2',3',6',7'-tetra(2-methylbutyloxy)spirobifluoren]-ylene is in a wavelength range from 400 to 490 nm.

For the purposes of this application, a green-emitting recurring unit G is defined in such a way that the maximum of the fluorescence or phosphorescence curve of a film of a polymer which contains 10 mol % of this unit G and 90 mol % of 2,7-[2',3',6',7'-tetra(2-methylbutyloxy)spirobifluoren]yl-ene is in a wavelength range from 490 to 570 nm.

For the purposes of this application, a red-emitting recurring unit R is defined in such a way that the maximum of the fluorescence or phosphorescence curve of a film of a polymer which contains 10 mol % of this unit R and 90 mol % of 2,7-[2',3',6',7'-tetra(2-methylbutyloxy)spirobifluoren]-ylene is in a wavelength range from 570 to 700 nm.

It should expressly be pointed out here that, for the purposes of this invention, mixed colours, such as, for example, yellow or orange, are also to be ascribed to red or green emission, depending on their emission maximum.

Suitable blue-emitting recurring units B are typically units which are generally used as polymer backbone or those which are used as blue emitters. These are generally those which have at least one aromatic or other conjugated structure, but do not shift the emission colour into the green or red. Preference is given to aromatic structures having 4 to 40 C atoms, but also stilbene and tolan derivatives and certain bis(styryl)arylene derivatives. These would be, for example, the following structural elements, which may be substituted or unsubstituted: 1,4-phenylene, 1,4-naphthylene, 1,4- or 9,10-anthracenylene, 2,7- or 3,6-phenanthrenylene, 4,4'-biphenylylene, 4,4"-terphenylylene, 4,4'-bi-1,1'-naphthylylene, 4,4'-stilbene derivatives, 4,5-dihydropyrene derivatives, 4,5,9,10-tetrahydropyrene derivatives (for example as described in EP 0 699 699), fluorene derivatives (for example as described in EP 0 842 208, WO 99/54385, WO 00/22027, WO 00/22026, WO 00/46321), spirobifluorene derivatives (for example as described in EP 0 707 020, EP 0 894 107, WO 03/020790, WO 02/077060), 5,7-dihydrodibenzoxepine derivatives, cis- and trans-indenofluorene derivatives (for example as described in WO 2004/041901 and WO 2004/113412) and 9,10-dihydrophenanthrene derivatives (for example as described in WO 2005/014689). Besides these classes, the so-called ladder PPPs (LPPPs) (for example as described in WO 92/18552), but also PPPs containing ansa structures (for example as described in EP 0 690 086), for example, are also suitable here. Bis(styryl)arylene derivatives which are not electron-rich can also be used for this purpose.

It may also be preferred for more than one blue-emitting recurring unit B of this type to be used in a polymer.

If the polymer, in addition to the units of the formula I, contains further green-emitting recurring units G, suitable units for this purpose are preferably those which have at least one aromatic or other conjugated structure and shift the emission colour into the green. Preferred structures for green-emitting recurring units G are selected from the groups of the electron-rich bisstyrylarylenes and derivatives of these structures. Without wishing to be tied to a particular theory here, an electron-donating substitution results in a green shift of the emission. Further preferred green-emitting recurring units are selected from the groups of the benzothiadiazoles and corresponding oxygen derivatives, the quinoxalines, the phenothiazines, the phenoxazines, the dihydrophenazines, the bis(thio-phenyl)arylenes, the oligo(thiophenylenes) and the phenazines. It is also permissible here to use a plurality of different recurring units of this type instead of one green-emitting recurring unit G, in which case the total proportion of the green-emitting recurring units G is at most 3 mol %.

Particularly preferred structures which are suitable as green-emitting recurring units G are structures of the following formulae:

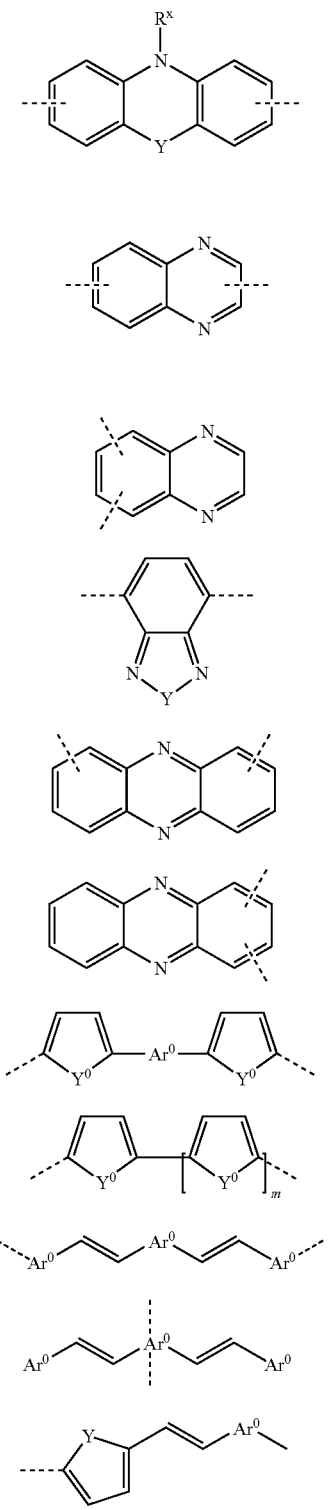

(LVIII)
(LIX)
(LX)
(LXI)
(LXII)
(LXIII)
(LXIV)
(LXV)
(LXVI)
(LXVII)
(LXVIII)

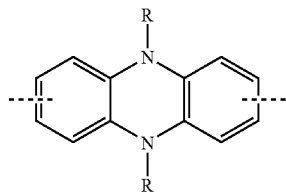

(LXIX)

which may be substituted or unsubstituted, where the following applies to the symbols and indices used:

$Y^0$ is preferably on each occurrence, identically or differently, S or O;

$Ar^0$ is on each occurrence, identically or differently, an arylene group selected from the groups of the phenylenes, biphenylenes, fluorenylenes, spirobifluorenylenes, thienylenes, furanylenes, pyrrolylenes, with the proviso that at least one $Ar^0$ unit in the formulae (LXVI) and (LXVII) must be an electron-rich aromatic unit; this is achieved by selecting this unit from the structures of the substituted or unsubstituted thionylenes, furanylenes or pyrrolylenes or by this unit being a phenylene group which is substituted by at least one alkoxy, aryloxy or substituted or unsubstituted amino group or also a plurality of identical or different groups of this type;

$R^x$ is preferably on each occurrence, identically or differently, H, a straight-chain, branched or cyclic alkyl chain having 1 to 22 C atoms, in which, in addition, one or more non-adjacent C atoms may be replaced by O, S, —CO—O— or —O—CO—O—, where one or more H atoms may also be replaced by fluorine, a substituted or unsubstituted aryl group having 5 to 40 C atoms, in which, in addition, one or more C atoms may be replaced by O, S or N;

m is on each occurrence, identically or differently, 1, 2, 3, 4 or 5, preferably 1, 2 or 3;

the dashed bonds here are intended to indicate the link in the polymer; they do not stand for a methyl group here.

Suitable red-emitting recurring units R are preferably units which have at least one aromatic or other conjugated structure and shift the emission colour into the red. Preferred structures for red-emitting recurring units R are those in which electron-rich units, such as, for example, thiophene, are combined with green-emitting electron-deficient units, such as, for example, quinoxaline or benzothiadiazole. Further preferred red-emitting recurring units R are systems comprising at least four condensed aromatic units, such as, for example, rubrenes, pentacenes or perylenes, which are preferably substituted, or preferably conjugated push-pull systems (systems which are substituted by donor and acceptor substituents) or systems such as squarines or quinacridones, which are preferably substituted. It is also permissible here for a plurality of recurring units of this type to be used instead of one red-emitting recurring unit R, in which case the total proportion of the red-emitting recurring units R is at most 1 mol %.

Particularly preferred structures which are suitable as red-emitting recurring units R are structures of the following formulae:

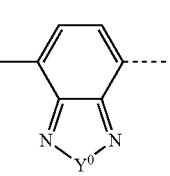

(LXX)

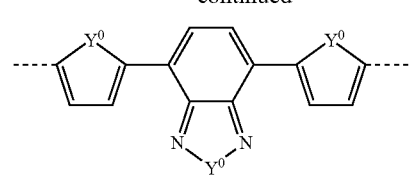
(LXXI)

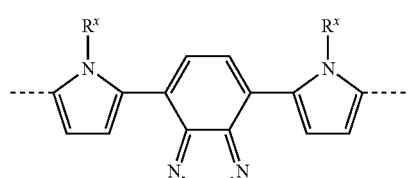
(LXXII)

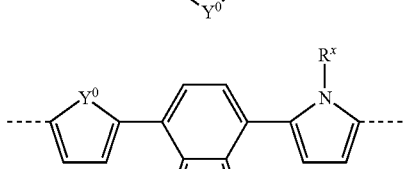
(LXXIII)

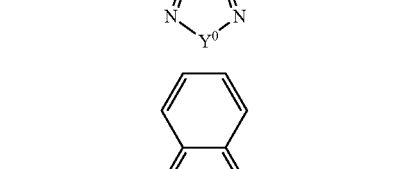
(LXXIV)

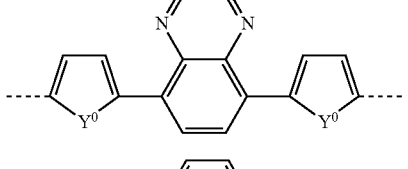
(LXXV)

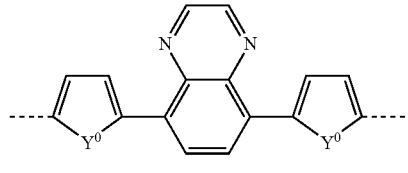
(LXXVI)

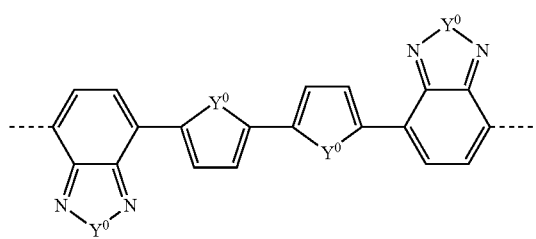
(LXXVII)

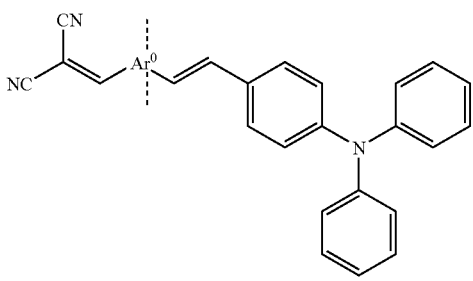

which may be substituted or unsubstituted, where the symbols and indices have the same meaning as described above.

Suitable blue-, green- and red-emitting structural units B, G and R are in principle also units which emit light from the triplet state, i.e. exhibit electrophosphorescence instead of electrofluorescence, which frequently causes an increase in the energy efficiency. These units are referred to below as triplet emitters. The use of metal complexes of this type in low-molecular-weight OLEDs is described, for example, in M. A. Baldo et al (*Appl. Phys. Lett.* 1999, 75, 4-6). Suitable for this purpose are firstly compounds which contain heavy atoms, i.e. atoms from the Periodic Table of the Elements having an atomic number of greater than 36. Particularly suitable for this purpose are compounds containing d and f transition metals which satisfy the above-mentioned condition. Very particular preference is given here to corresponding structural units which contain elements from groups 8 to 10 (i.e. Ru, Os, Rh, Ir, Pd, Pt). Suitable structural units for the polymers according to the invention are, for example, various complexes which are described, for example, in WO 02/068435, DE 101 16 962, EP 1 239 526 and WO 2004/026886. Corresponding monomers are described in WO 02/068435.

The colours of the complexes here are determined primarily by the metal used, by the precise ligand structure and by the substituents on the ligand.

Both green- and red-emitting complexes are known. Thus, for example, an unsubstituted tris(phenylpyridyl)iridium(III) emits green light, whereas electron-donating substituents in the para-position to the coordinating carbon atom (for example diarylamino substituents) shift the emission into the orange-red. Furthermore, derivatives of this complex having a varied ligand structure which result directly (without further substitutions) in orange or dark-red emission are known. Examples of such ligands are 2-phenylisoquinoline, 2-benzothiophenylpyridine or 2-naphthylpyridine.

Blue-emitting complexes are obtained, for example, by substituting the tris(phenylpyridyl)iridium(III) parent structure by electron-withdrawing substituents, such as, for example, a plurality of fluorine and/or cyano groups.

The polymers according to the invention are generally prepared by polymerisation of one or more types of monomer, at least one monomer of which is described by the formula I. Suitable polymerisation reactions are known to the person skilled in the art and are described in the literature. Particularly suitable and preferred polymerisation reactions, all of which result in C—C links, are the following:

(A) SUZUKI polymerisation;
(B) YAMAMOTO polymerisation;
(C) STILLE polymerisation.

The way in which the polymerisation can be carried out by these methods and the way in which the polymers can then be separated off from the reaction medium and purified are known to the person skilled in the art and are described in detail in the literature, for example in WO 03/048225 or WO 2004/037887.

The C—C linking reactions are preferably selected from the groups of the SUZUKI coupling, the YAMAMOTO coupling and the STILLE coupling.

The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6, WO 02/07343 A1 or WO 2005/026144 A1.

For the synthesis of the polymers and dendrimers, the corresponding monomers are required. The synthesis of the above-described units from groups 1 to 4 and of type R, G and B is known to the person skilled in the art and is described in the literature, for example in WO 2005/014689, WO 2005/030827 and WO 2005/030828. These and the literature cited therein are incorporated into the present application by way of reference.

It may additionally be preferred to use polymers or dendrimers according to the invention not as the pure substance, but instead as a blend (mixture) together with further polymeric, oligomeric, dendritic or low-molecular-weight substances of any desired type. These may, for example, improve the electronic properties or emit themselves. The present invention therefore also relates to blends of this type.

The term "blend" refers above and below to a mixture comprising at least one oligomeric or polymeric component.

The invention furthermore relates to solutions and formulations comprising one or more compounds, polymers, dendrimers, blends or mixtures according to the invention in one or more solvents. The way in which solutions of this type can be prepared is known to the person skilled in the art and is described, for example, in WO 02/072714, WO 03/019694 and the literature cited therein.

These solutions can be used in order to produce thin polymer layers, for example by area-coating methods (for example spin coating) or by printing processes (for example ink-et printing).

Compounds of the formula I, polymers or dendrimers containing structural units of the formula I which contain one or more groups $X^1$-Sp- as described above are particularly suitable for the production of films or coatings, in particular for the production of structured coatings, for example by thermal or tight-induced in-situ polymerisation and in-situ crosslinking, such as, for example, in-situ UV photopolymerisation or photopatterning. For such applications, particular preference is given to compounds, polymers or dendrimers according to the invention containing one or more groups $X^1$-Sp-, in which $X^1$ denotes acrylate, methacrylate, vinyl, epoxide or oxetane. Both corresponding compounds of the formula I and polymers thereof can be used as the pure substance here; however, it is also possible to use mixtures, formulations or blends of these compounds/polymers as described above. These can be used with or without addition of solvents and/or binders. Suitable materials, processes and apparatuses for the methods described above are described, for example, in WO 2005/083812. Possible binders are, for example, polystyrene, polycarbonate, polyacrylates, polyvinylbutyral and similar, optoelectronically neutral polymers.

Suitable and preferred solvents are, for example, toluene, anisole, xylene, methylbenzoates, dimethylanisole, mesitylene, tetralin, veratrol and tetrahydrofuran.

The polymers, dendrimers, blends and formulations according to the invention can be used in PLEDs. The way in which PLEDs can be produced is known to the person skilled in the art and is described in detail, for example, as a general process in WO 2004/070772, which should be adapted correspondingly for the individual case.

As described above, the materials according to the invention are very particularly suitable as electroluminescent materials in PLEDs or displays produced in this way.

For the purposes of the present invention, electroluminescent materials are taken to mean materials which can be used as active layer in a PLED. Active layer means that the layer is capable of emitting light on application of an electric field (tight-emitting layer) and/or that it improves the injection and/or transport of the positive and/or negative charges (charge-injection or charge-transport layer).

The present invention therefore also relates to the use of polymers, dendrimers or blends according to the invention in a PLED, in particular as electroluminescent material.

The present invention thus likewise relates to a PLED having one or more active layers, where at least one of these active layers comprises one or more polymers or dendrimers according to the invention. The active layer can be, for example, a light-emitting layer and/or a transport layer and/or a charge-injection layer.

The present application text and also the examples below are directed to the use of materials according to the invention in relation to PLEDs and corresponding displays. In spite of this restriction of the description, it is possible for the person skilled in the art, without further inventive step, also to use the materials according to the invention as semiconductors for further uses in other electronic devices, for example in organic field-effect transistors (OFETs), in organic integrated circuits (O-ICs), in organic thin-film transistors (O-TFTs), in organic solar cells (O-SCs), in organic laser diodes (O-lasers), in organic photovoltaic (OPV) elements or devices or in organic photoreceptors (OPCs), to mention but a few applications.

The present invention likewise relates to the use of materials according to the invention in the corresponding devices.

It is likewise easy for the person skilled in the art to apply the descriptions given above for conjugated polymers to conjugated dendrimers without further inventive step. The present invention thus also relates to conjugated dendrimers of this type.

The following examples are intended to explain the invention without restricting it. In particular, the features, properties and advantages described therein of the defined compounds on which the particular example is based can also be applied to other compounds which are not indicated in detail, but fall within the scope of protection of the claims, unless stated otherwise elsewhere.

EXAMPLE 1

Compound (1) is prepared as follows:

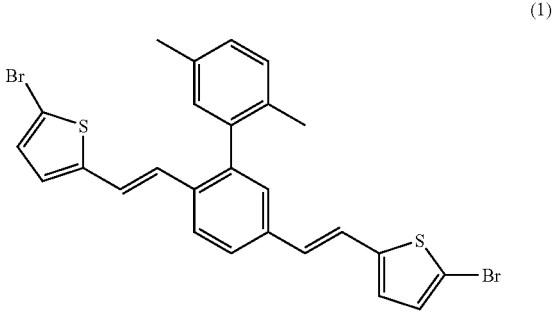

(1)

1.1 Preparation of diethyl[5-(diethoxyphosphorylmethyl)-2',5'-di-methylbiphenyl-2-ylmethyl]phosphonate

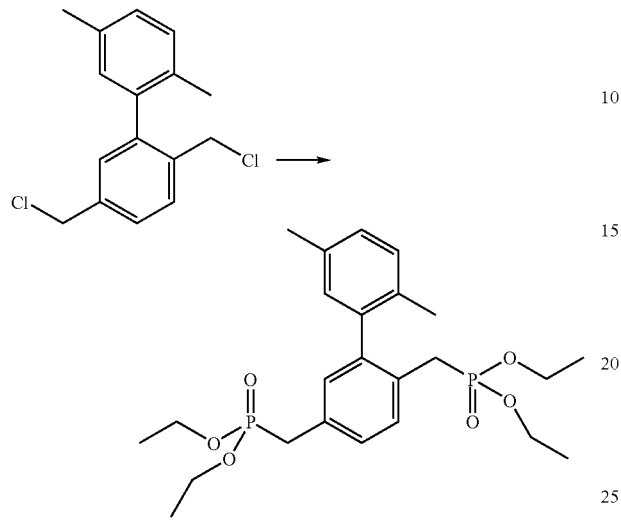

50 g (180 mmol) of 2',5'-bis-chloromethyl-2,5-dimethylbiphenyl are heated at 160° C. in 63 ml (366 mmol) of triethyl phosphite until the evolution of gas is complete. The residue which remains is employed in the subsequent reaction without further purification.

1.2 Preparation of 1,4-bis(-2-bromo-5-vinylthiophenyl)-2-(2,6-di-methylphenyl)benzene

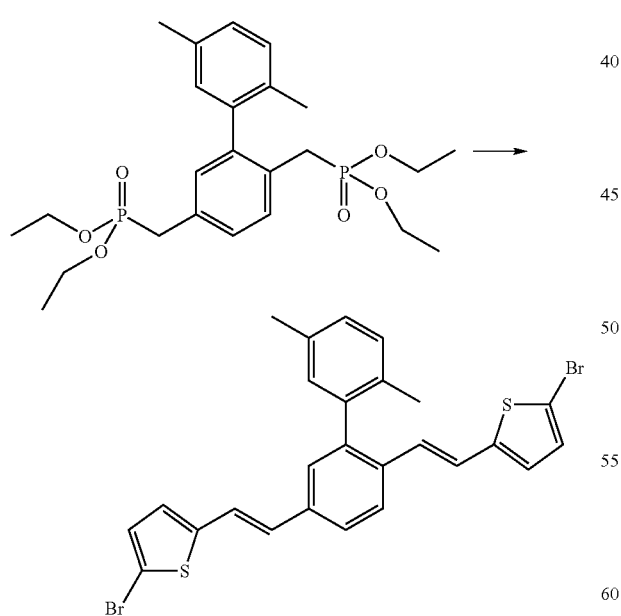

31.8 g (65.5 mmol) of diethyl[5-(diethoxyphosphorylmethyl)-2',5'-dimethyl-biphenyl-2-ylmethyl]phosphonate are initially introduced in 225 ml of DMF, 25.18 g (262 mmol) of NaO$^t$Bu are added at about 5° C. under a protective gas, and, after a stirring time of 30 minutes at 5° C., a solution of 25 g (131 mmol) of 2-bromothiophene-5-carbaldehyde in 60 ml of DMF is added dropwise at 5° C. over the course of 15 minutes. After 1 hour, 75 ml of 4 M HCl are added dropwise at about 5° C., and the precipitate is filtered off with suction, washed with MeOH and dried. Recrystallisation seven times from EtOH/toluene (4+1) gives the product in the form of pale-yellow crystals having a purity of >99.8% (determined by RP-HPLC) and a yield of 28.8 g (79%).

EXAMPLE 2

Compound (2) is prepared as follows:

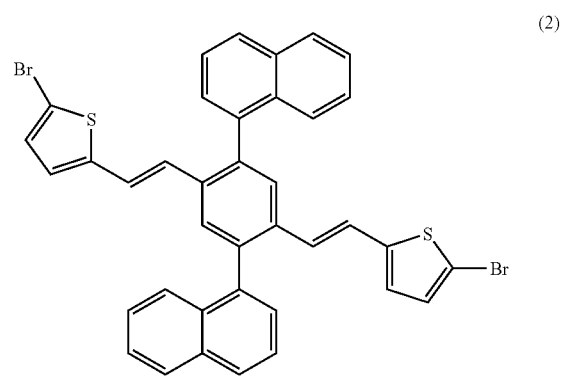

(2)

2.1 Preparation of diethyl[4-(diethoxyphosphorylmethyl)-2,6-dinaphthalen-1-ylbenzyl]phosphonate

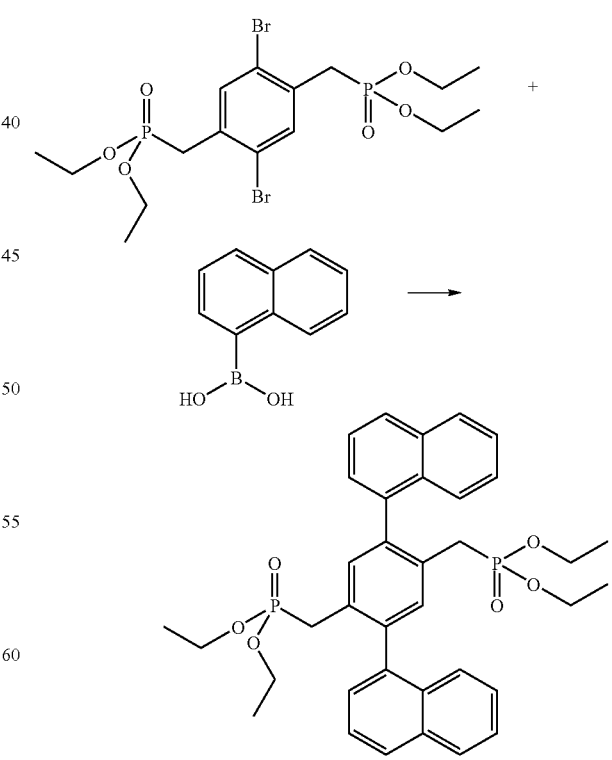

A mixture of 6.97 g (13 mmol) of diethyl [2,5-dibromo-4-(diethoxy-phosphorylmethyl)benzyl]phosphonate, 4.7 g (27.3 mmol) of naphthylboronic acid, 16.9 g (52 mmol) of Cs$_2$CO$_3$ and 90 mg (0.4 mmol) of Pd(OAc)$_2$ is suspended in 75 ml of dried dioxane and saturated with nitrogen for 30 minutes. 160 mg (0.8 mmol) of P(t-Bu)$_3$ are subsequently added, and the mixture is heated at the boil for 2 hours. After cooling, the mixture is partitioned between water and ethyl acetate, the organic phase is washed a number of times with water and dried over Na$_2$SO$_4$, and the solvent is removed in vacuo. Column chromatography gives 7.2 g (88%) of the di-phosphonate as a pale-yellow foam.

2.2 Preparation of 1,4-bis(-2-bromo-5-vinylthiophenyl)-2,6-(1-naphthyl)benzene

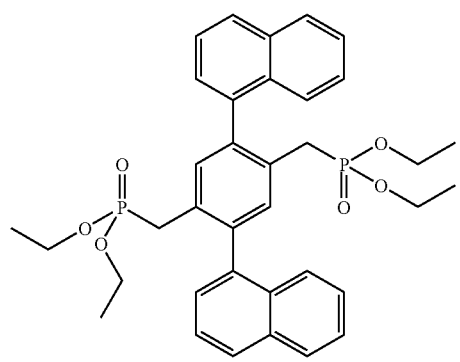

8.2 g (13 mmol) of the diphosphonate are dissolved in 60 ml of dry DMF, and the solution is cooled to 5° C. 5.0 g (52 mmol) of NaO$^t$Bu are subsequently added in small portions, 5.5 g (28.6 mmol) of 2-bromothiophene-5-carboxaldehyde in 20 ml of DMF are added dropwise, and the mixture is stirred at 5° C. for 1 hour. 25 ml of 4 M HCl are subsequently added dropwise, and the precipitate is filtered off with suction, washed with H$_2$O, ethanol and heptane and recrystallised from ethanol/toluene (1+5), giving the product in the form of yellow crystals having a purity of >99.9% (RP-HPLC) and a yield of 6.6 g (72%).

EXAMPLES 3 TO 7

Polymers P1 to P4 according to the invention and comparative polymer C1 are synthesised by SUZUKI coupling as described in WO 03/048225. The composition of synthesised polymers P1 to P4 and of comparative polymer C1 is as follows:

Polymer P1:

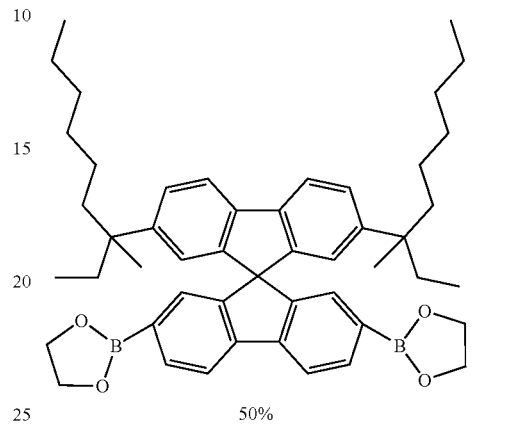

50%

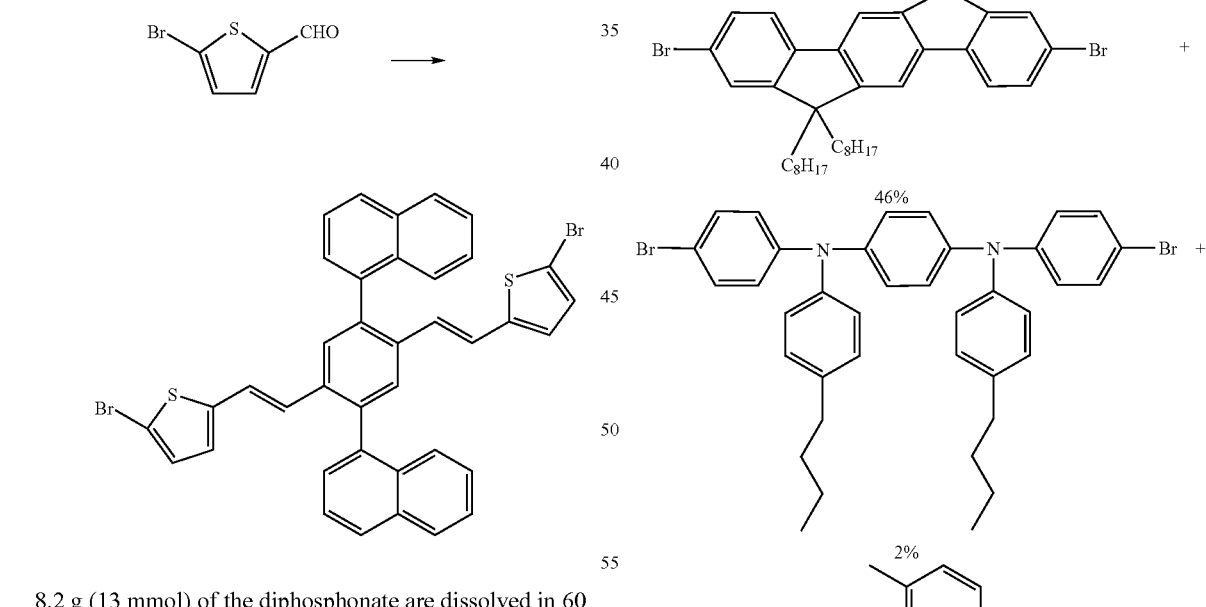

46%

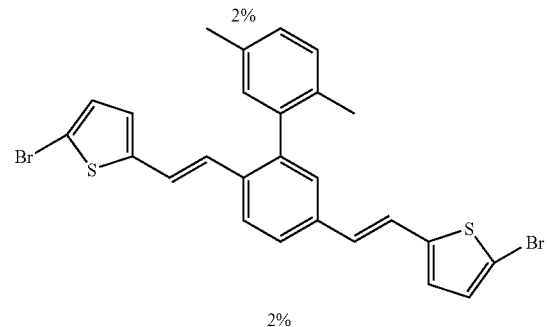

2%

Polymer P2:
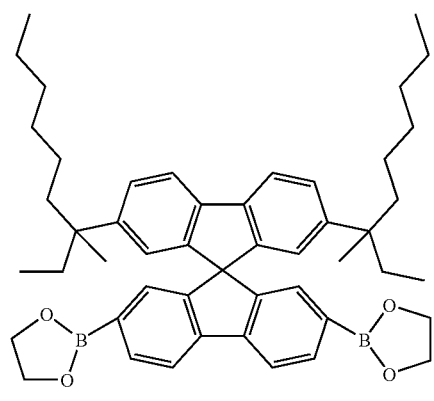
50%
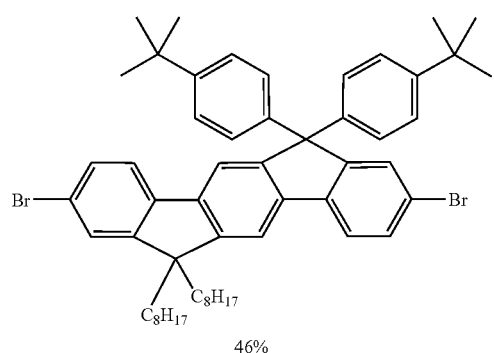
46%
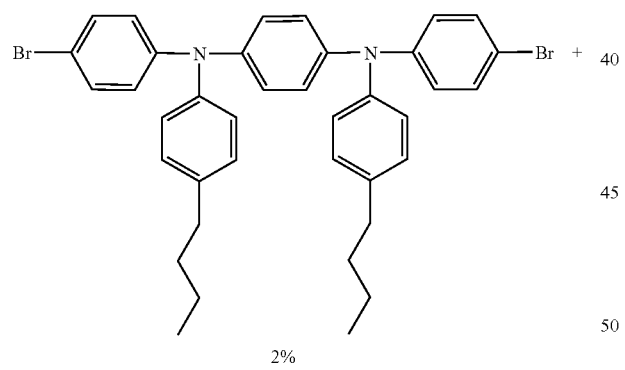
2%
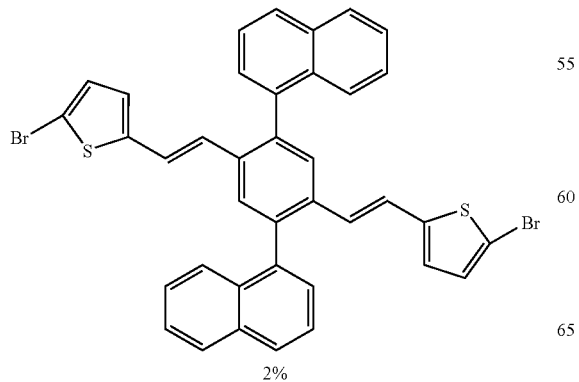
2%
Polymer P3:
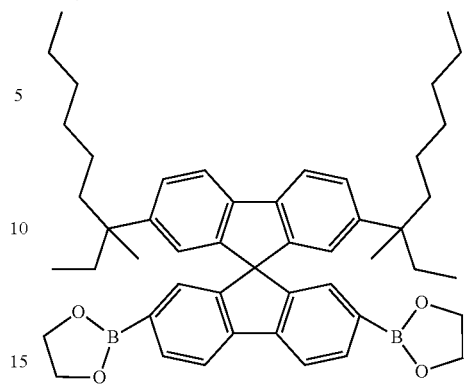
50%
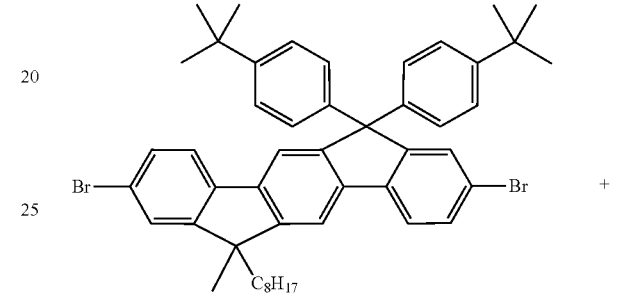
46%
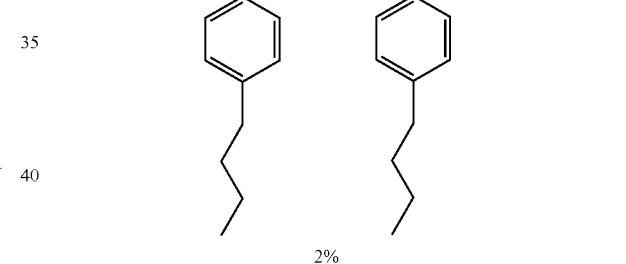
2%
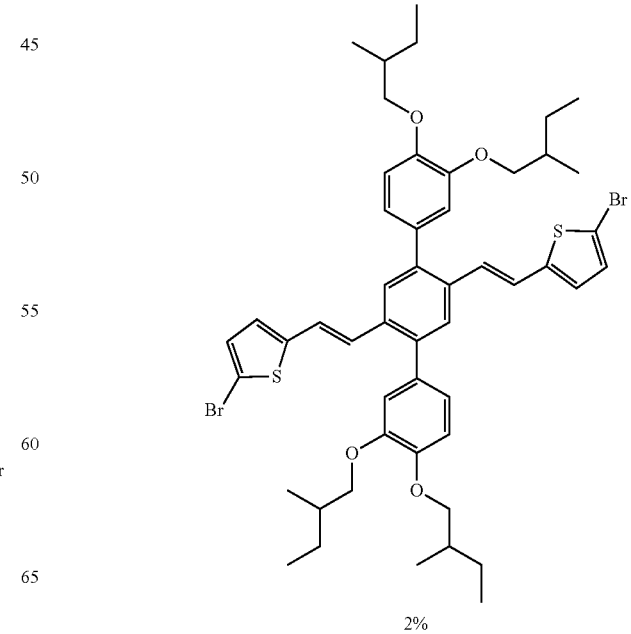
2%

Polymer P4:
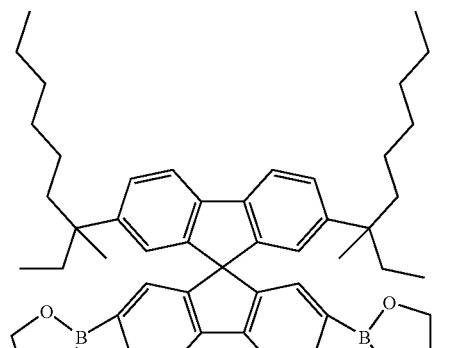
50%
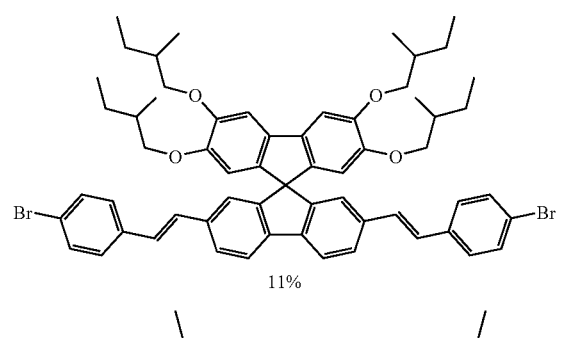
11%
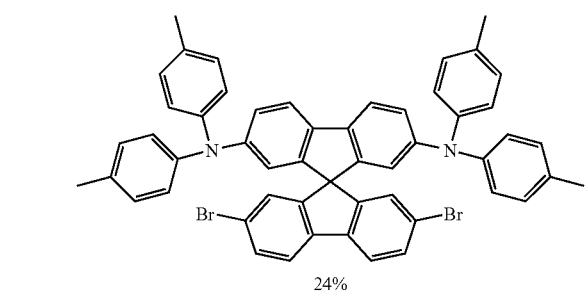
24%
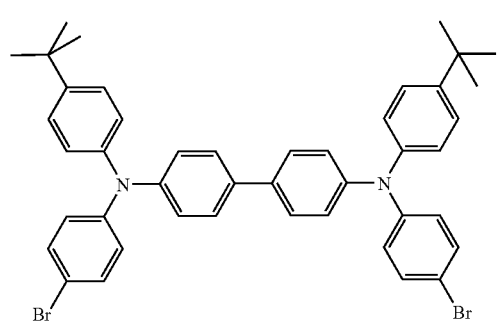
5%
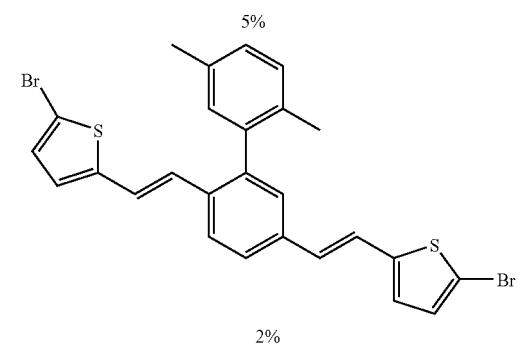
2%
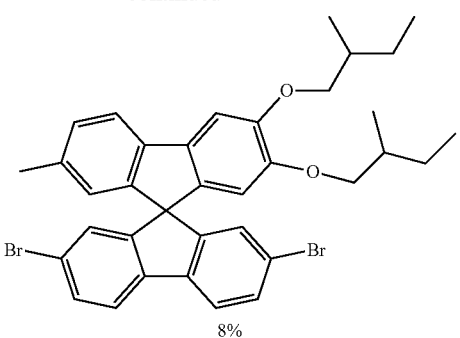
8%
Comparative Polymer C1:
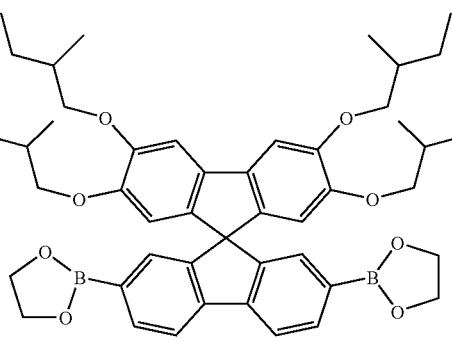
50%
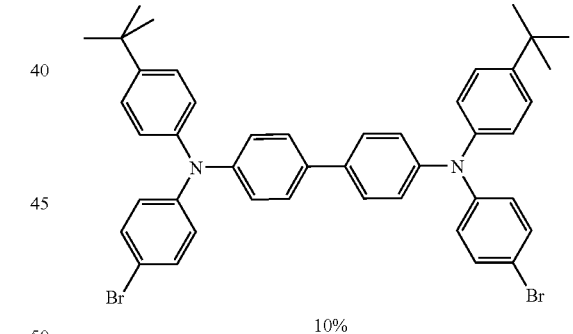
10%
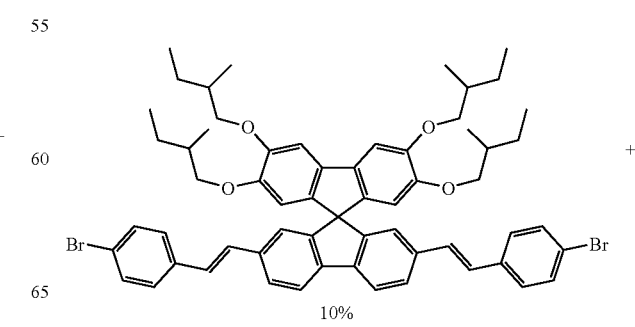
10%

-continued

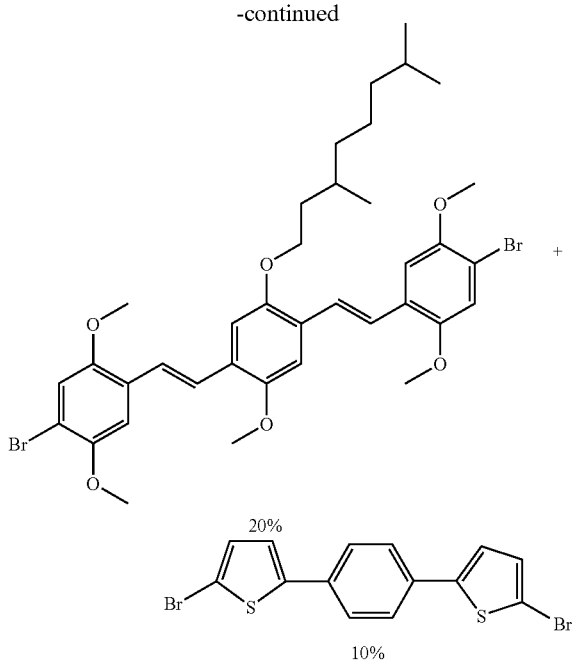

EXAMPLES 8 TO 12

Device Examples

Production of a PLED

The production of a polymeric light-emitting diode has already been described many times in the patent literature (see, for example, WO 04/037887). In order to explain the present invention by way of example, PLEDs comprising polymers P1 to P4 and comparative polymer C1 are produced by spin coating onto ITO substrates which have been coated in advance with PEDOT and a hole-injecting interlayer. (PEDOT is a polythiophene derivative (Baytron P, from H. C. Starck, Goslar)). The layer thickness of the polymer layer is about 80 nm. A Ba/Al cathode (metals from Aldrich) is then applied by vapour deposition, and the PLED is encapsulated and characterised in electro-optical terms.

The results obtained on use of polymers P1 to P4 and C1 in PLEDs are shown in Table 1.

As can be seen from the results, the efficiency of the polymers according to the invention is better than that of the comparative polymer. The emission colour is comparable and the lifetimes are significantly improved taking this into account. This shows that the polymers according to the invention are more suitable for use in displays than polymers in accordance with the prior art.

| Ex. | Polymer | Max. eff. [Cd/A] | U@100 cd/m² [V] | CIE [x/y] | Lifetime [h] |
|---|---|---|---|---|---|
| 8 | P1 | 17.10 | 4.77 | 0.31/0.59 | 372@6000 |
| 9 | P2 | 17.38 | 4.89 | 0.32/0.60 | 159@6000 |
| 10 | P3 | 17.09 | 4.63 | 0.34/0.59 | 100@6000 |
| 11 | P4 | 8.98 | 3.17 | 0.33/0.60 | 560@2000[a] |
| 12 | C1 | 11.08 | 2.86 | 0.33/0.59 | 323@1500 |

[a]MUX64, 100 Hz, no counterpulse

The invention claimed is:

1. A compound of formula (I)

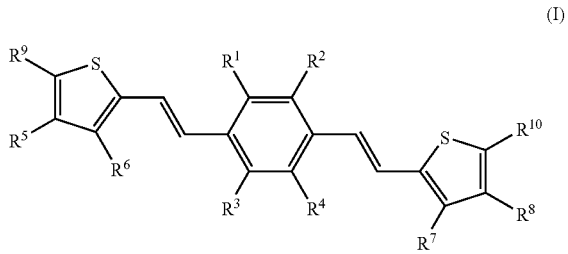

wherein $R^1$, $R^2$, $R^3$, $R^4$, $R^5$, $R^6$, $R^7$, $R^8$, $R^9$, and $R^{10}$
are, independently of one another, H; $X^1$; $X^1$-Sp-; —CN; —NO$_2$; —NCS; —NCO; —OCN; —SCN; —SF$_5$; —Si(R)$_3$; a straight-chain, branched or cyclic alkyl or alkoxy group having 1 to 22 C atoms wherein one or more non-adjacent C atoms are optionally replaced by —C(R)=C(R)—, —C≡C—, —N(R)—, —O—, —S—, —CO—, —CO—O—, —O—CO—, or —O—CO—O—, and one or more H atoms are optionally replaced by fluorine; an aryl, aryloxy, heteroaryl or heteroaryloxy group having 5 to 40 C atoms, each of which is optionally substituted by one or more of non-aromatic radicals $R^1$, $R^2$, $R^3$, $R^4$, $R^5$, $R^6$, $R^7$, $R^8$, $R^9$, and $R^{10}$; wherein two or more of radicals $R^1$, $R^2$, $R^3$, $R^4$, $R^5$, $R^6$, $R^7$, $R^8$, $R^9$, and $R^{10}$ together optionally define an aliphatic or aromatic, mono- or polycyclic ring system and which optionally also define a condensed ring system with the benzene ring or a thiophene ring of the compound of formula (I);

R is, identically or differently on each occurrence, H; halogen; a straight-chain, branched or cyclic alkyl chain having 1 to 22 C atoms wherein one or more non-adjacent C atoms are optionally replaced by —O—, —S—, —CO—, —CO—O—, —O—CO—, or —O—CO—O—, and one or more H atoms are optionally replaced by fluorine; and an aryl, aryloxy, heteroaryl or heteroaryloxy group having 5 to 40 C atoms optionally substituted by one or more of non-aromatic radicals $R^1$, $R^2$, $R^3$, $R^4$, $R^5$, $R^6$, $R^7$, $R^8$, $R^9$, and $R^{10}$; wherein a plurality of radicals R with one another and/or with further radicals $R^1$, $R^2$, $R^3$, $R^4$, $R^5$, $R^6$, $R^7$, $R^8$, $R^9$, and $R^{10}$ optionally define an aromatic or aliphatic, mono- or polycyclic ring system and which optionally also define a condensed ring system with the benzene ring or a thiophene ring of the compound of formula (I);

$X^1$ is, identically or differently on each occurrence, CH$_2$=CW$^1$—COO —, CH$_2$=CW$^1$—CO—,

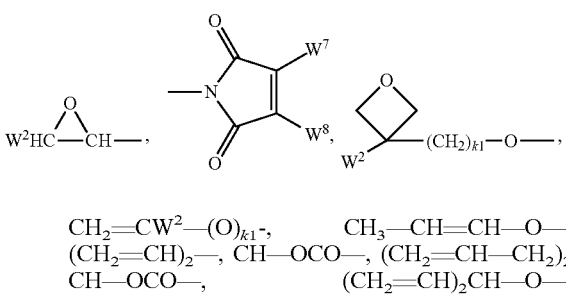

CH$_2$=CW$^2$—(O)$_{k1}$-,   CH$_3$—CH=CH—O—,
(CH$_2$=CH)$_2$—,   CH—OCO—,   (CH$_2$=CH—CH$_2$)$_2$
CH—OCO—,   (CH$_2$=CH)$_2$CH—O—, (CH$_2$=CH—CH$_2$)$_2$N—, (CH$_2$=CH—CH$_2$)$_2$N—CO—, HO—CW$^2$W$^3$—, HS—CW$^2$W$^3$—, HW$^2$N—, HO—CW$^2$W$^3$—NH—, CH$_2$=CW$^1$—CO—NH—, CH$_2$=CH—(COO)$_{k1}$—Phe-(O)$_{k2}$—, CH$_2$=CH—(CO)$_{k1}$-Phe-(O)$_{k2}$—Phe-CH=CH—, HOOC—, OCN— and W$^4$W$^5$W$^6$Si—, wherein W$^1$ is H, F, Cl, CN, CF$_3$, phenyl, or alkyl having 1 to 5 C atoms, W$^2$ and W$^3$ each, independently of one another, are H or alkyl having 1 to 5 C atoms, W$^4$, W$^5$, and W$^6$ each, independently of one another, are Cl, oxaalkyl, or oxacarbonylalkyl having 1 to 5 C atoms, W$^7$ and W$^8$ each, independently of one another, are H, Cl, or alkyl having 1 to 5 C atoms, Phe is 1,4-phenylene, which is optionally substituted by one or more radicals L, and k$_1$ and k$_2$ each, independently of one another, are 0 or 1;

L is, identically or differently on each occurrence, F, Cl, Br, I, —CN, —NO$_2$, —NCO, —NCS, —OCN, —SCN, —C(=O)N(R)$_2$, —C(=O)Y$^1$, —C(=O)R, —N(R)$_2$, wherein R is as defined above and Y$^1$ is halogen, optionally substituted silyl, aryl having 4 to 40 C atoms, or straight-chain or branched alkyl, alkoxy, alkylcarbonyl, alkoxycarbonyl, alkylcarbonyloxy, or alkoxycarbonyloxy having 1 to 22 C atoms, wherein one or more H atoms are optionally replaced by F or Cl;

Sp is, identically or differently on each occurrence, selected from the formula Sp'-X', so that X$^1$-Sp- is X$^1$-Sp'-X'-, wherein Sp' is an alkylene having 1 to 20 C atoms optionally mono- or polysubstituted by F, Cl, Br, I, or CN and wherein one or more non-adjacent CH$_2$ groups are optionally replaced, independently of one another, by —O—, —S—, —NH—, —NR$^o$—, —SiR$^o$R$^{oo}$—, —CO—, —COO—, —OCO—, —OCO—O—, —S—CO—, —CO—S—, —NR$^o$—CO—O—, —O—CO—NR$^o$—, —NR$^o$—CO—NR$^o$—, —CH=CH—, or —C≡C— in such a way that O and/or S atoms are not linked directly to one another, X' is —O—, —S—, —CO—, —COO—, —OCO—, —O—COO—, —CO—NR$^o$—, —NR$^o$—CO—, —NR$^o$—CO—NR$^o$—, —OCH$_2$—, —CH$_2$O—, —SCH$_2$—, —CH$_2$S—, —CF$_2$O—, —OCF$_2$—, —CF$_2$S—, —SCF$_2$—, —CF$_2$CH$_2$—, —CH$_2$CF$_2$—, —CF$_2$CF$_2$—, —CH=N—, —N=CH—, —N=N—, —CH=CR$^o$—, —CY$^2$=CY$^3$—, —C≡C—, —CH=CH—COO—, —OCO—CH=CH—, or a single bond, R$^o$ and R$^{oo}$ each, independently of one another, are H or an alkyl having 1 to 12 C atoms, and Y$^2$ and Y$^3$ each, independently of one another, are H, F, Cl or CN;

wherein at least one of the radicals R$^1$, R$^2$, R$^3$, and R$^4$ is an optionally substituted aryl or heteroaryl group.

2. The compound of claim 1, wherein R$^9$ and R$^{10}$ are, independently of one another, X$^1$.

3. The compound of claim 1, wherein one, two, three, or four of the radicals R$^1$, R$^2$, R$^3$, and R$^4$ is an optionally substituted alkyl group having 1 to 22 C atoms or an optionally substituted aryl or heteroaryl group having 5 to 40 C atoms, wherein the radicals R$^1$, R$^2$, R$^3$, and R$^4$ that are not an optionally substituted alkyl group having 1 to 22 C atoms or an optionally substituted aryl or heteroaryl group having 5 to 40 C atoms are H.

4. The compound of claim 3, wherein the radicals R$^1$, R$^2$, R$^3$, and R$^4$ which are not H are phenyl or 1-naphthyl, each of which is optionally substituted by one or more radicals L, wherein L is selected from the group consisting of F, Cl, Br, I, —CN, —NO$_2$, —NCO, —NCS, —OCN, —SCN, —C(=O)N(R)$_2$, —C(=O)Y$^1$, —C(=O)R, and —N(R)$_2$, wherein Y$^1$ is halogen, optionally substituted silyl, aryl having 4 to 40 C atoms, and straight-chain or branched alkyl, alkoxy, alkylcarbonyl, alkoxycarbonyl, alkylcarbonyl-oxy or alkoxycarbonyloxy having 1 to 22 C atoms, wherein one or more H atoms may optionally be replaced by F or Cl.

5. The compound of claim 3, wherein the radicals R$^1$, R$^2$, R$^3$, and R$^4$ which are not H are optionally fluorinated straight-chain, branched or cyclic alkyl having 1 to 22 C atoms.

6. The compound of claim 1, wherein said compound is selected from one of the following sub-formulae:

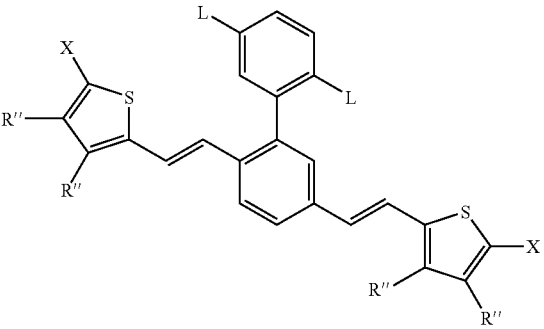

(Ia)

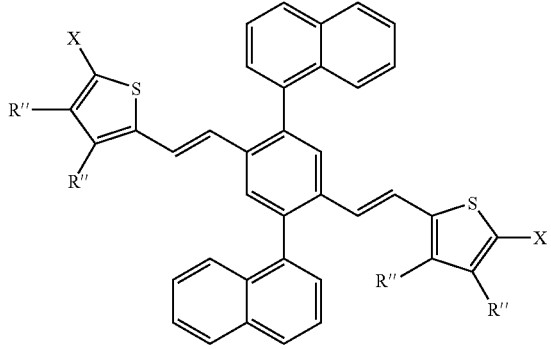

(Ib)

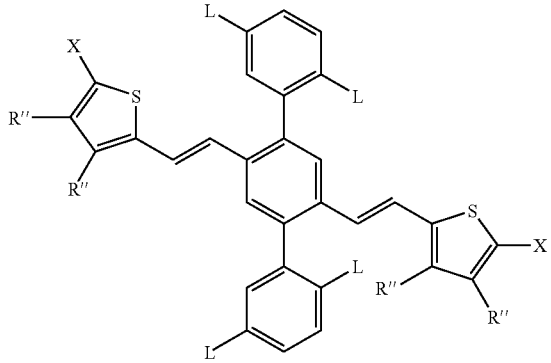

(Ic)

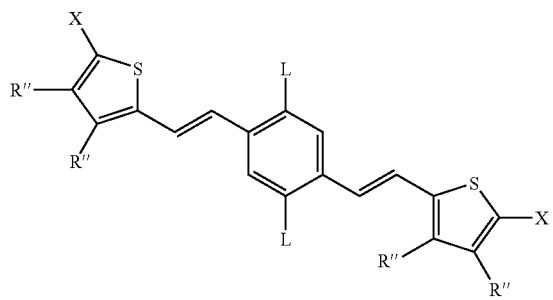

(Id)

wherein

R″ are, independently of one another, H; $X^1$; $X^1$-Sp-; —CN; —NO$_2$; —NCS; —NCO; —OCN; —SCN; —SF$_5$; —Si(R)$_3$; a straight-chain, branched or cyclic alkyl or alkoxy group having 1 to 22 C atoms wherein one or more non-adjacent C atoms are optionally replaced by —C(R)=C(R)—, —C≡C—, —N(R)—, —O—, —S—, —CO—, —CO—O—, —O—CO—, or —O—CO—O—, and one or more H atoms are optionally replaced by fluorine; an aryl, aryloxy, heteroaryl or heteroaryloxy group having 5 to 40 C atoms, each of which is optionally substituted by one or more of non-aromatic radicals $R^1$, $R^2$, $R^3$, $R^4$, $R^5$, $R^6$, $R^7$, $R^8$, $R^9$, and $R^{10}$; wherein two or more of radicals $R^1$, $R^2$, $R^3$, $R^4$, $R^5$, $R^6$, $R^7$, $R^8$, $R^9$, and $R^{10}$ together optionally define an aliphatic or aromatic, mono- or polycyclic ring system and which optionally also define a condensed ring system with the benzene ring or a thiophene ring of the compound of formula (I); and L is selected from the group consisting of F, Cl, Br, I, —CN, —NO$_2$, —NCO, —NCS, —OCN, —SCN, —C(=O)N(R)$_2$, —C(=O)$Y^1$, —C(=O)R, and —N(R)$_2$, wherein $Y^1$ is halogen, optionally substituted silyl, aryl having 4 to 40 C atoms, and straight-chain or branched alkyl, alkoxy, alkylcarbonyl, alkoxycarbonyl, alkyl carbonyloxy or alkoxycarbonyloxy having 1 to 22 C atoms, wherein one or more H atoms may optionally be replaced by F or Cl.

7. A polymer or dendrimer prepared from one or more compounds of claim 1, wherein one or more of $R^2$, $R^3$, $R^4$, $R^5$, $R^6$, $R^7$, $R^8$, $R^9$, and $R^{10}$ is a link in said polymer or dendrimer.

8. The polymer or dendrimer of claim 7, wherein said polymer or dendrimer comprises further structural elements selected from the group consisting of fluorenylenes; spirobifluorenylenes; dihydrophenanthrenylenes; tetrahydropyrenylenes; stilbenylenes; bisstyrylarylenes; 1,4-phenylenes; 1,4-naphthylenes ; 1,4-anthrylenes; 9,10- anthrylenes ; 1,6-pyrenylenes ; 2,7-pyrenylenes ; 4,9-pyrenylenes ; 3,9-perylenylenes; 3,10-perylenylenes; 2,7-phenanthrenylenes; 3,6-phenanthrenylenes; 4,4'-biphenylylenes; 4,4"-terphenylylenes; and 4,4'-bi- 1,1 '-naphthylylenes.

9. The polymer or dendrimer of claim 7, wherein said polymer or dendrimer comprises further structural elements selected from the group consisting of triarylamines, triarylphosphines, benzidines, tetraarylene-para-phenylenediamines, phenothiazines, phenoxazines, dihydrophenazines, thianthrenes, dibenzo-p-dioxins, phenoxathiynes, carbazoles, azulenes, thiophenes, pyrroles, and furans.

10. The polymer or dendrimer of claim 7, wherein said polymer or dendrimer comprises further structural elements selected from the group consisting of pyridines, pyrimidines, pyridazines, pyrazines, anthracenes, triarylboranes, oxadiazoles, quinolines, quinoxalines, and phenazines.

11. The polymer or dendrimer of claim 7, wherein said polymer or dendrimer comprises
  at least 50 mol % of further structural elements selected from the group consisting of fluorenylenes; spirobifluorenylenes; dihydrophenanthrenylenes; tetrahydropyrenylenes; stilbenylenes; bisstyrylarylenes; 1,4-phenylenes; 1,4-naphthylenes; 1,4-anthrylenes; 9,10-anthrylenes; 1,6-pyrenylenes; 2,7-pyrenylenes; 4,9-pyrenylenes; 3,9-perylenylenes; 3,10-perylenylenes; 2,7-phenanthrenylenes; 3,6-phenanthrenylenes; 4,4'-biphenylylenes; 4,4"-terphenylylenes; and 4,4'-bi-1,1'-naphthylylenes; and
  2 to 30 mol % of further structural elements selected from the group consisting of triarylamines, triarylphosphines, benzidines, tetraarylene-para-phenylenediamines, phenothiazines, phenoxazines, dihydrophenazines, thianthrenes, dibenzo-p-dioxins, phenoxathiynes, carbazoles, azulenes, thiophenes, pyrroles, furans, pyridines, pyrimidines, pyridazines, pyrazines, anthracenes, triarylboranes, oxadiazoles, quinolines, quinoxalines, and phenazines.

12. The polymer or dendrimer of claim 7, wherein said polymer or dendrimer comprises from 0.01 to 25 mol % of units derived from compounds of formula (I).

13. A blend comprising one or more polymers or dendrimers of claim 7 and optionally one or more further polymeric, oligomeric, dendritic, or low-molecular-weight substances.

14. A mixture of low-molecular-weight compounds comprising one or more compounds of claim 1 and one or more light-emitting and/or polymerisable compounds.

15. A formulation comprising one or more compounds of claim 1 and one or more solvents and/or polymeric binders.

16. An electro-optical or electronic device comprising one or more compounds of claim 1.

17. The device of claim 16, wherein said device is an organic or polymeric organic light-emitting diode, a field-effect transistor, an organic thin-film transistor, an organic integrated circuit, an organic solar cell, an organic laser diode, an organic photovoltaic element or device, or an organic photoreceptor.

18. A process for preparing the compound of claim 1, comprising heating optionally substituted 1,4-dihalophenyl with trialkyl phosphite to form a phosphonate and reacting said phosphonate with optionally substituted 2-bromothiophene-5-carbaldehyde in the presence of a base.

* * * * *